(12) United States Patent
Casola et al.

(10) Patent No.: US 9,504,701 B2
(45) Date of Patent: Nov. 29, 2016

(54) METHODS FOR TREATING VIRAL INFECTIONS USING HYDROGEN SULFIDE DONORS

(71) Applicants: Antonella Casola, Galveston, TX (US); Olivier Escaffre, Galveston, TX (US); Alexander N. Freiberg, League City, TX (US); Roberto P. Garofalo, Galveston, TX (US)

(72) Inventors: Antonella Casola, Galveston, TX (US); Olivier Escaffre, Galveston, TX (US); Alexander N. Freiberg, League City, TX (US); Roberto P. Garofalo, Galveston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 14/941,340

(22) Filed: Nov. 13, 2015

(65) Prior Publication Data

US 2016/0058779 A1    Mar. 3, 2016

Related U.S. Application Data

(63) Continuation-in-part of application No. 14/728,737, filed on Jun. 2, 2015.

(60) Provisional application No. 62/006,680, filed on Jun. 2, 2014.

(51) Int. Cl.
| | | |
|---|---|---|
| A61K 31/10 | (2006.01) | |
| A61K 33/04 | (2006.01) | |
| A61K 31/675 | (2006.01) | |
| A61K 45/06 | (2006.01) | |
| A61K 31/385 | (2006.01) | |
| A61K 31/404 | (2006.01) | |
| A61K 31/5375 | (2006.01) | |

(52) U.S. Cl.
CPC ............ *A61K 31/675* (2013.01); *A61K 31/10* (2013.01); *A61K 31/385* (2013.01); *A61K 31/404* (2013.01); *A61K 31/5375* (2013.01); *A61K 33/04* (2013.01); *A61K 45/06* (2013.01)

(58) Field of Classification Search
CPC .............................. A61K 31/10; A61K 33/04
See application file for complete search history.

(56) References Cited

U.S. PATENT DOCUMENTS

| 8,541,396 B2 | 9/2013 | Moore et al. .................. 514/90 |
| 2015/0342969 A1 | 12/2015 | Casola et al. .................. 514/90 |

OTHER PUBLICATIONS

Bao et al., "Airway epithelial cell response to human metapneumovirus infection", 2007, Virology 368:91-101.
Casola et al., "Oxidant tone regulates RANTES gene expression in airway epithelial cells infected with respiratory syncytial virus. Role in viral-induced interferon regulatory factor activation", 2001, J Biol Chem 276:19715-22.
Garofalo et al., "Transcriptional activation of the interleukin-8 gene by respiratory syncytial virus infection in alveolar epithelial cells: nuclear translocation of the RelA transcription factor as a mechanism producing airway mucosal inflammation", 1996, J Virol 70:8773-81.
Hosakote et al., "Viral-mediated inhibition of antioxidant enzymes contributes to the pathogenesis of severe respiratory syncytial virus bronchiolitis", 2011, Am J Respir Crit Care Med 183:1550-60.
Jackson et al., "Human sulfide:quinone oxidoreductase catalyzes the first step in hydrogen sulfide metabolism and produces a sulfane sulfur metabolite", 2012, Biochemistry 51:6804-15.
Olszewska-Pazdrak et al., "Cell-specific expression of RANTES, MCP-1, and MIP-1alpha by lower airway epithelial cells and eosinophils infected with respiratory syncytial virus", 1998, J Virol 72:4756-64.
Pazdrak et al., "MAPK activation is involved in posttranscriptional regulation of RSV-induced RANTES gene expression", 2002, Am J Physiol Lung Cell Mol Physiol 283:L364-L372.
Zhang et al., "Expression of respiratory syncytial virus-induced chemokine gene networks in lower airway epithelial cells revealed by cDNA microarrays", 2001, J Virol 75:9044-58.

*Primary Examiner* — Samira Jean-Louis
(74) *Attorney, Agent, or Firm* — Norton Rose Fulbright US LLP

(57) ABSTRACT

Certain embodiments are directed to methods of treating respiratory infection by administering an $H_2S$ donor.

7 Claims, 29 Drawing Sheets

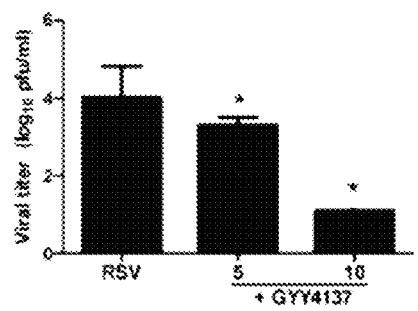
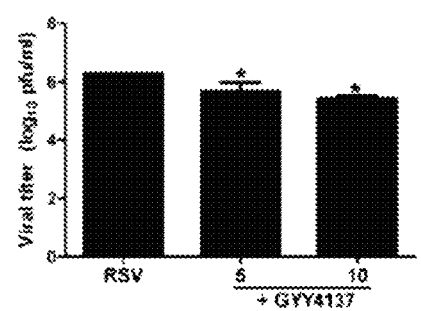
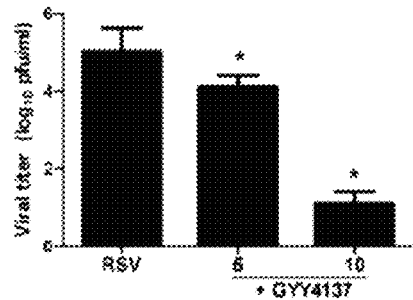
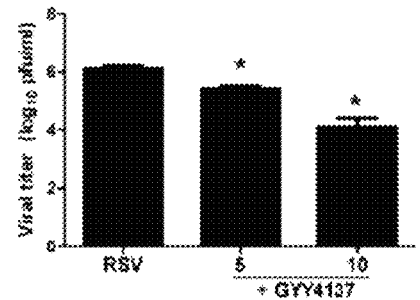
FIG. 6D-6E

SEQUENCE LISTING

<160> NUMBER OF SEQ ID NOS: 9

<210> SEQ ID NO 1
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 1
ctgcgatgag tggcaggctt tttttttttt aactcaaagc tc                42

<210> SEQ ID NO 2
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 2
ctgcgatgag tggcaggc                                           18

<210> SEQ ID NO 3
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 3
actacagtgt attagacttr acagcagaag                              30

<210> SEQ ID NO 4
<211> LENGTH: 48
<212> TYPE: DNA
<213> ORGANISM: Artificial Sequence
<220> FEATURE:
<223> OTHER INFORMATION: synthetic oligonucleotide

<400> SEQUENCE: 4
ctgcgatgag tggcaggcac tacagtgtat tagacttrac agcagaag          48

<210> SEQ ID NO 5
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 5
gcatcttctc catgraattc agg                                     23

<210> SEQ ID NO 6
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 6
aggtttgccc tgagggatg                                          20

<210> SEQ ID NO 7
<211> LENGTH: 20
<212> TYPE: DNA
<213> ORGANISM: Artificial Sequence

```
<220> FEATURE:
<223> OTHER INFORMATION: synthetic oligonucleotide

<400> SEQUENCE: 7
ggagtgctcc ggtggctttt                                                   20

<210> SEQ ID NO 8
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 8
agcggcttcc tgctctctga                                                   20

<210> SEQ ID NO 9
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 9
cagctcaggc tggcccttta                                                   20
```

METHODS FOR TREATING VIRAL INFECTIONS USING HYDROGEN SULFIDE DONORS

This application is a continuation in part of U.S. application Ser. No. 14/728,737, filed Jun. 2, 2015, which claims the benefits of U.S. provisional application Ser. No. 62/006,680 filed Jun. 2, 2014. The contents of the referenced applications are incorporated into the present application by reference.

STATEMENT REGARDING FEDERALLY FUNDED RESEARCH

This invention was made with government support under AI062885, AI07924602, and P30 ES006676 awarded by the National Institutes of Health. The government may have certain rights in the invention.

REFERENCE TO SEQUENCE LISTING

A sequence listing required by 37 CFR 1.821-1.825 is being submitted electronically with this application. The sequence listing is incorporated herein by reference.

BACKGROUND

Viral infections are very common and cause substantial suffering and hundreds of millions of dollars of economic loss every year. The prevention of viral infections is typically accomplished by administering antiviral vaccines. However, vaccines still cannot effectively prevent an outbreak or epidemic because viruses easily mutate rendering the vaccine ineffective. Some treatments such as interferon or interleukin-2 therapy can inhibit virus replication and improve cell-mediated immune function, but are expensive and are associated with adverse reactions in some instances.

Group V—negative-sense single strand RNA viruses ("Group V") comprise many human pathogens. These viruses have significantly higher mutation rates compared to DNA viruses generally. The higher mutation rates correlate with faster rates of developing resistance to treatments. Thus, there is a constant need for additional treatments for these viruses.

Group V viruses include many viruses that cause respiratory infections in humans. Respiratory infections, particularly upper respiratory infections ("URIs") are spread through air and through direct contact by touching of hands to infected surfaces and then touching hands to eyes, nose, or mouth. The nasopharynx, nasal passages, and sinus cavities all play an important role in filtering and housing the majority of these pathogens.

Respiratory Syncytial Virus (RSV) is one pathogen that infects the respiratory tract of humans. RSV is a member of the genus Pneumovirus of the family Paramyxoviridae. Human RSV (HRSV) is the leading cause of severe lower respiratory tract disease in young children and is responsible for considerable morbidity in the elderly and immunocompromised patients. Due to incomplete resistance to RSV in the infected host after a natural infection, RSV may infect multiple times during childhood and adult life. Human metapneumovirus (hMPV) is also a pneumovirus, belonging to the Paramyxoviridae family, which cause a spectrum of diseases similar to RSV, although it is less common than RSV. There is no vaccine or treatment available for either of these infections.

Group V viruses also include viruses in the Bunyaviridae family, which include devastating viral pathogens such as Hantavirus, Crimean-Congo hemorrhagic fever virus, and Rift Valley fever virus (RVFV). As an example, RVFV is a devastating mosquito-borne viral zoonotic disease that causes serious morbidity and mortality in both humans and livestock for which no prophylactic or therapeutic measures are available.

Filoviruses such as Ebola virus are another family of Group V viruses. Each year, Ebola claims many human lives and decimate gorilla populations in Africa. Infection results in an acute fever often associated with profuse internal and external bleeding and death rates of up to 90%.

There is a need for additional methods for the regulation of viral infections and host defenses.

SUMMARY

Certain embodiments are directed to methods of treating Group V—negative-sense single strand RNA virus illnesses. In certain aspects a hydrogen sulfide ($H_2S$) releasing compound ($H_2S$ donor) is administered to a subject having, suspected of having, or at risk of acquiring a Group V virus induced illness. A subject at risk of acquiring a Group V virus induced illness is a subject that has been exposed, or was or is in an environment where he/she is exposed to a Group V virus that can infect a human.

Certain embodiments are directed to methods of treating respiratory infections. In certain aspects a hydrogen sulfide ($H_2S$) releasing compound ($H_2S$ donor) is administered to a subject having, suspected of having, or at risk of acquiring a respiratory infection. A subject at risk of acquiring a respiratory infection is a subject that has been exposed, or was or is in an environment where he/she is exposed to a virus that can infect the pulmonary tract.

Certain embodiments are directed to methods for treating a viral infection of the respiratory tract of a subject comprising administering an effective amount of a $H_2S$ donor to the subject. In certain aspects the viral infection is a paramyxovirus or orthomyxovirus infection. In certain aspects the paramyxovirus is respiratory syncytial virus (RSV), Nipah virus, or human metapneumovirus (hMPV), or the orthomyxovirus is Influenzavirus A, Influenzavirus B, or Influenzavirus C virus. The subject can be suspected of having a respiratory tract infection, be diagnosed with a respiratory tract infection, or suspected of being exposed to a respiratory virus. A subject suspected of being exposed is a subject that was present in a location that was known to have a current outbreak of a virus, historically is associated with the presence of a virus (e.g., an endemic area for the virus or a hospital setting), or was subsequently identified as having active virus present (e.g., a battle field associated with bioweapons or geographic location later associated with an outbreak).

Certain embodiments are directed to methods for treating a mononegavirales infection comprising administering an effective amount of a $H_2S$ donor to the subject. In certain aspects the viral infection is a filoviridae infection. In certain aspects the viral infection is an Ebola virus infection. The subject can be suspected of having a mononegavirales infection, be diagnosed with a mononegavirales infection, or suspected of being exposed to a mononegavirales virus. A subject suspected of being exposed is a subject that was present in a location that was known to have a current outbreak of a virus, historically is associated with the presence of a virus (e.g., an endemic area for the virus or a hospital setting), or was subsequently identified as having active virus present (e.g., a battle field associated with bioweapons or geographic location later associated with an outbreak).

Certain embodiments are directed to methods for treating a bunyaviridae infection comprising administering an effective amount of a $H_2S$ donor to the subject. In certain aspects the viral infection is a Rift Valley fever virus infection. The subject can be suspected of having a bunyaviridae infection, be diagnosed with a bunyaviridae infection, or suspected of being exposed to a bunyaviridae virus. A subject suspected of being exposed is a subject that was present in a location that was known to have a current outbreak of a virus, historically is associated with the presence of a virus (e.g., an endemic area for the virus or a hospital setting), or was subsequently identified as having active virus present (e.g., a battle field associated with bioweapons or geographic location later associated with an outbreak).

In certain aspects an $H_2S$ donor is administered by intravenous injection, inhalation/inspiration into the respiratory tract, or taken orally. The $H_2S$ donor can be a slow release $H_2S$ donor, a fast release $H_2S$ donor, or a combination of a slow release $H_2S$ donor and a fast release $H_2S$ donor. In certain instance the slow and fast release donor are separate molecules. In other aspects the slow and fast donor attributes can be associated with a single molecule or formulation. In certain aspects the slow release donor is administered within 1, 2, 3, 4, 5, 6, 7, 8, 9, 10 minutes or hours before or after the administration of a fast release donor. In other aspects a fast release donor is administered within 1, 2, 3, 4, 5, 6, 7, 8, 9, 10 minutes or hours after the administration of a slow release donor. In certain aspects the ratio of fast release donor to slow release donor administered or in a formulation can be 1:20, 1:10, 1:5, 1:4, 1:2, 1:1, 2:1, 4:1, 5:1, 10:1 or 20:1 including all values and ranges there between. In certain aspects the $H_2S$ donor is Gyy4137, ACS67, diallyl trisulfide, NaHS, ATB-343, ATB-337, AP67, or combinations thereof.

Other embodiments of the invention are discussed throughout this application. Any embodiment discussed with respect to one aspect of the invention applies to other aspects of the invention as well and vice versa. Each embodiment described herein is understood to be an embodiment of the invention that is applicable to other aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIG. 6A-6G. Effect of $H_2S$ donor treatment on different steps of viral replication. A549 cells were infected with RSV for 1 h and then incubated in the presence or absence of GYY4137 for 24 h. (A to C) Cells were harvested to prepare either total RNA to measure viral genome copy numbers (A) or RSVN gene copy numbers (B) by qRT-PCR or total cell lysates to measure viral protein expression by Western blotting (C). The membrane was stripped and reprobed with β-actin as a control for equal loading of the samples. Data are representative of data from three independent experiments with similar results. (D) A549 cells were infected with RSV for 1 h and then incubated in the presence or absence of GYY4137 at 5 and 10 mM for 24 h. Cell supernatants (left) and cell pellets (right) were harvested separately to determine viral titers by a plaque assay. Results are expressed as means±standard errors and are representative of data from three independent experiments run in triplicate. *, P 0.05 compared to untreated RSV-infected cells. (E) HEp-2 cells were infected with RSV at an MOI of 0.01 in the presence or absence of GYY4137 at 5 and 10 mM for 48 h. Cell supernatants (left) and cell pellets (right) were harvested separately to determine viral titers by a plaque assay. Results are expressed as means±standard errors and are representative of two independent experiments run in triplicate. *, P<0.05 compared to untreated RSV-infected cells. (F) A549 cells were infected with RSV for 1 h and then incubated in the presence or absence of GYY4137 for 24 h. Cell supernatants were harvested to measure viral protein expression by Western blotting. Data are representative of data from two independent experiments with similar results. (G) Light microscopy photograph (magnification, ×20) of HEp-2 cells infected with RSV at an MOI of 0.01 for 48 h in the presence (right) or absence (left) of GYY4137 at 10 mM. The arrow indicates one of the many syncytia present in the cell monolayer as a result of viral infection.

DESCRIPTION

Figures 1A, 1B, 1C:
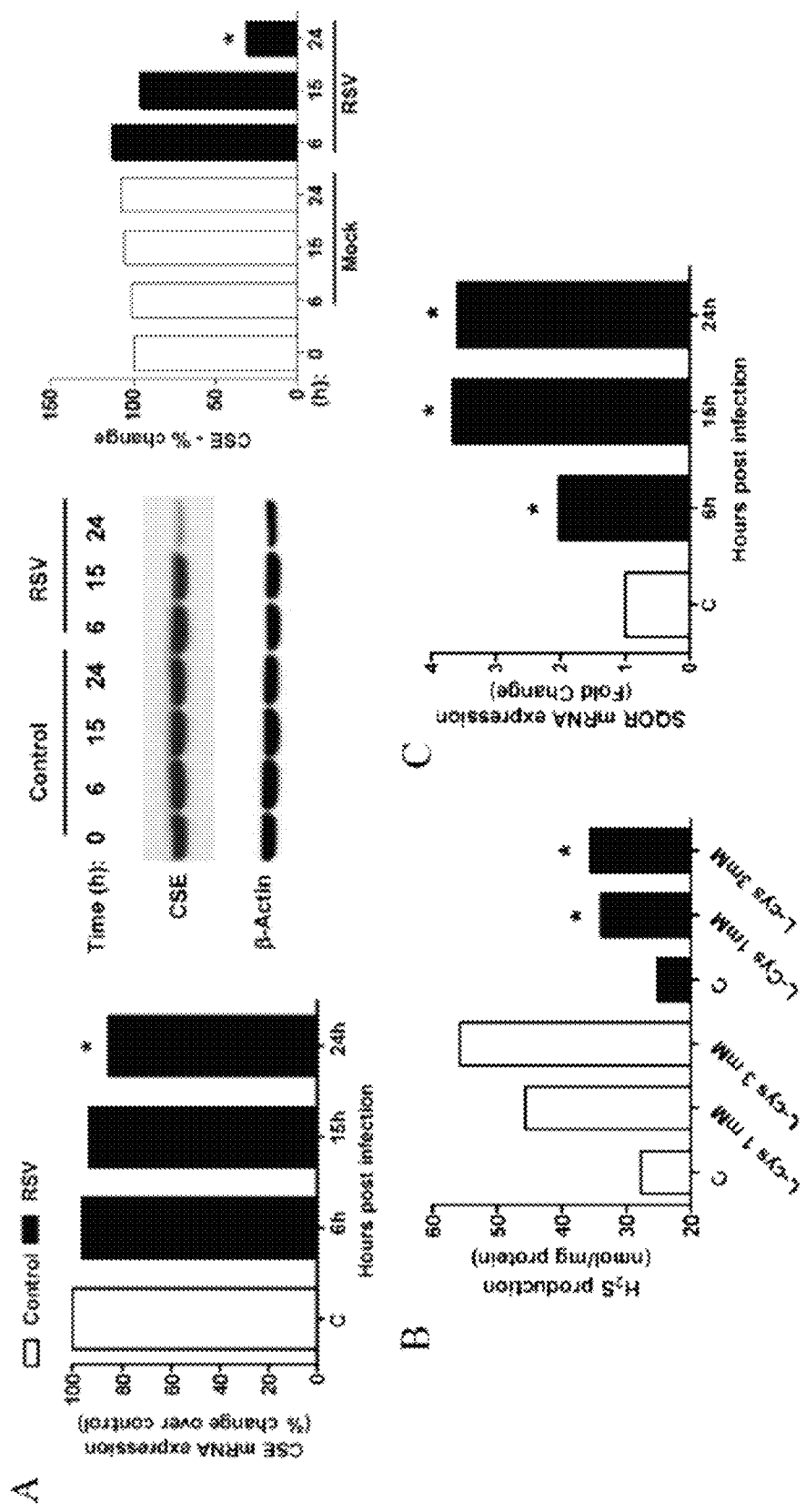
FIG. 1A-1D. Effect of RSV infection on $H_2S$ production in airway epithelial cells. A549 cells were infected with RSV for 6, 15, and 24 h and harvested to prepare total RNA or total cell lysates. (A and C) CSE (A, left) and SQOR (C) mRNA levels in uninfected and RSV-infected cells were measured by reverse transcriptase quantitative PCR (qRT-PCR). CSE cellular levels were also measured by Western blotting of total cell lysates. The membrane was stripped and reprobed for β-actin to determine equal loading of the samples (A, middle). Densitometric analysis of CSE band intensity, normalized to β-actin, was performed by using Alpha Ease software version 2200 (2.2d) (Alpha Innotech Co., San Leandro, Calif.) (A, right). Results are representative of data from three independent experiments. *, P<0.05 compared to uninfected cells. (B) A549 cells were infected with RSV for 15 h and harvested to prepare total cell lysates. $H_2S$ production in uninfected and RSV-infected cells was determined by a methylene blue colorimetric assay. Results are representative of data from three independent experiments. *, P<0.05 compared to uninfected cells. (D) A549 cells were incubated with 5 μM the fluorescent probe SF7-AM and infected with RSV for 1 h. Medium or 10 mM GYY4137 was added to uninfected or infected cells and incubated for 15 h. (Left) Images of uninfected and untreated cells (control) and uninfected or infected cells treated with 10 mM GYY4137. (Right) Average fluorescence intensity quantified by confocal microscopy using Zeiss Metamorph software. Results are representative of data from three independent experiments. *, P<0.05 compared to uninfected, treated cells.

There are many illnesses caused by viruses. Group V—negative-sense single strand RNA viruses encompasses many of the known human viral pathogens. As a non-limiting example, about 75 percent of acute respiratory illnesses are caused by viruses. Human respiratory syncytial virus and adenovirus are two of the most common viruses that cause respiratory infections in both children and adults. Other Group V viruses include Filoviruses such as Ebola virus and Bunyaviruses such as Rift Valley fever virus.

I. Group V Negative-Sense Single-Stranded RNA Viruses

Group V negative sense strand RNA viruses are RNA viruses that use RNA that is complementary to mRNA (negative sense). Before translation of the RNA genome can occur, a complementary RNA (positive sense) must be created by RNA polymerase. These viruses have a high mutational rate in comparison to DNA viruses because the viral RNA polymerase lacks a proof-reading ability. The high mutation rate correlates to faster development of resistance to treatments.

Group V viruses include one order, eight families, and several unassigned genera and species. The order Mononegavirales includes viruses in the: Bornaviridae family such as Borna disease virus; Filoviridae family; Nyamiviridae such as Nyavirus; Paramyxoviridae family such as Hendra virus, Measles virus, Mumps virus, NDV, Nipah virus, and RSV; and Rhabdoviridae such as Rabies virus. Additional unassigned Group V virus families include Arenav, Bunyaviridae, Ophioviridae, and Orthomyxoviridae. Additional unassigned Group V virus genera include: Deltavirus such as Hepatitis D virus; Dichorhavirus; Emaravirus; Nyavirus such as Nyamanini and Midway viruses; Tenuivirus; and Varicosavirus. Additional unassigned Group V virus species include *Taastrup* virus and *Sclerotinia sclerotiorum* negative-stranded RNA virus 1. Additional details for some of the Group V viruses follow.

A. Respiratory Viruses

Respiratory viruses are those viruses that infect the respiratory tract of an animal and include paramyxoviruses and orthomyxoviruses. Examples of respiratory viruses include respiratory syncytial virus, human metapneumovirus, adenovirus, and influenza.

Paramyxoviruses are negative-sense single-stranded RNA viruses responsible for a number of human and animal diseases. Their virions are enveloped and can be spherical, filamentous, or pleomorphic. Fusion proteins and attachment proteins appear as spikes on the virion surface. Matrix proteins inside the envelope stabilize the virus structure. The nucleocapsid core is composed of the genomic RNA, nucleocapsid proteins, phosphoproteins and polymerase proteins.

The genome is non-segmented negative-sense RNA, 15-19 kilobases in length and contains 6-10 genes. Non-coding regions of the viruses include a 3' leader sequence, typically 50 nucleotides in length, which acts as a transcriptional promoter; a 5' trailer sequence, 50-161 nucleotides long; and intergenomic regions between each gene, which vary in length from 1 to 56 nucleotides.

Gene order within the genome is conserved across the family due to a phenomenon known as transcriptional polarity in which genes closest to the 3' end of the genome are transcribed in greater abundance than those towards the 5' end, which is a result of the structure of the genome. After each gene is transcribed, the RNA-Dependent RNA polymerase pauses to release the new mRNA when it encounters an intergenic sequence. When the RNA polymerase is paused, there is a chance that it will dissociate from the RNA genome. If it dissociates, it must reenter the genome at the leader sequence, rather than continuing to transcribe the length of the genome. The result is that the further downstream genes are from the leader sequence the less likely they are to be transcribed by RNA polymerase. The typical gene sequence of paramyxoviruses is nucleocapsid (N)—phosphoprotein (P)—Matrix (M)—Fusion (F)—Attachment (H/HN/G)—Large (L). A number of important human diseases are caused by paramyxoviruses. These include mumps, measles, hRSV and hMPV.

The parainfluenza viruses are the second most common causes of respiratory tract disease in infants and children. They can cause pneumonia, bronchitis and croup in children and the elderly. Human metapneumovirus, initially described in about 2001, is also implicated in bronchitis, especially in children.

Paramyxoviruses are also responsible for a range of diseases in other animal species, for example canine distemper virus (dogs), phocine distemper virus (seals), cetacean morbillivirus (dolphins and porpoises), Newcastle disease virus (birds), and rinderpest virus (cattle). Some paramyxoviruses such as the henipaviruses are zoonotic pathogens, occurring naturally in an animal host, but also able to infect humans.

Human RSV (hRSV) is the leading cause of severe lower respiratory tract disease in young children and is responsible for considerable morbidity and mortality in humans. RSV is also recognized as an important agent of disease in immunocompromised adults and in the elderly. Due to incomplete resistance to RSV in the infected host after a natural infection, RSV may infect multiple times during childhood and adult life. The viral envelope is composed of a plasma membrane derived lipid bilayer that contains virally encoded structural proteins. A viral polymerase is packaged with the virion and transcribes genomic RNA into mRNA. The RSV genome encodes three transmembrane structural proteins, F, G, and SH, two matrix proteins, M and M2, three nucleocapsid proteins N, P, and L, and two nonstructural proteins, NS1 and NS2.

Fusion of HRSV and cell membranes is thought to occur at the cell surface and is a necessary step for the transfer of viral ribonucleoprotein into the cell cytoplasm during the early stages of infection. This process is mediated by the fusion (F) protein, which also promotes fusion of the membrane of infected cells with that of adjacent cells to form a characteristic syncytia, which is both a prominent cytopathic effect and an additional mechanism of viral spread.

HMPV is the second most common cause of lower respiratory tract infection in young children. The genomic organization of hMPV is analogous to RSV, however hMPV lacks the non-structural genes NS1 and NS2, and the hMPV antisense RNA genome contains eight open reading frames in slightly different gene order than RSV (viz. 3'-N-P-M-F-M2-SH-G-L-5'). hMPV is genetically similar to the avian pneumoviruses A, B and in particular type C.

The orthomyxoviruses are a family of RNA viruses that includes six genera: Influenza virus A, Influenza virus B, Influenza virus C, Isavirus, Thogotovirus and Quaranjavirus. The first three genera contain viruses that cause influenza in vertebrates, including birds, humans, and other mammals. Isaviruses infect salmon; the thogotoviruses are arboviruses, infecting vertebrates and invertebrates, such as ticks and mosquitoes. The three genera of Influenza virus are identified by antigenic differences in their nucleoprotein and matrix protein.

Viruses of this family contain 6 to 8 segments of linear negative sense RNA. The total genome length is 12000-15000 nucleotides (nt). The influenza A virus particle or virion is 80-120 nm in diameter and usually roughly spherical, although filamentous forms can occur. Typically, influenza is transmitted from infected mammals through the air by coughs or sneezes, creating aerosols containing the virus, and from infected birds through their droppings. Influenza can also be transmitted by saliva, nasal secretions, feces and blood. Infections occur through contact with these bodily fluids or with contaminated surfaces. Flu viruses can remain infectious for about one week at human body temperature, over 30 days at 0° C. (32° F.), and indefinitely at very low temperatures (such as lakes in northeast Siberia). They can be inactivated easily by disinfectants and detergents.

Influenza A viruses are classified based on viral surface proteins hemagglutinin (H) and neuraminidase (N). Sixteen H subtypes and nine N subtypes have been identified. Further variation exists; thus, specific influenza strain isolates are identified by a standard nomenclature specifying virus type, geographical location where first isolated, sequential number of isolation, year of isolation, and HA and NA subtype.

B. Filoviruses

Several Filoviruses cause severe diseases in humans and other primates. These viruses can cause hemorrhagic fevers. The Filoviruses form filamentous infectious viral particles, exclusively replicate in the cytoplasm of a host cell, have a genome of approximately 19 kb in length, and contains the following order of genes 3'-UTR-NP-VP35-VP40-GP-VP30-VP24-L-5'-UTR. Examples of Filoviruses include Ebola virus and Marburg virus. There are currently no vaccines for known filovirus.

C. Bunyaviruses

Several Bunyaviruses cause diseases in humans. These viruses are vector born viruses, which vectors include arthropods and mouse feces. Bunyaviruses genomes consist of a large, medium, and small RNA segments with a total genome size from about 10.5 to 22.7 kbp. Examples of Bunyaviruses include Bwamba Fever, California encephalitis virus, Crimean-Congo hemorrhagic fever, Hantavirus, and Rift Valley fever virus (RVFV). As an example, RVFV is a devastating mosquito-borne viral zoonotic disease that causes serious morbidity and mortality in both humans and livestock for which no prophylactic or therapeutic measures are available.

II. Hydrogen Sulfide as a Therapy for Viral Infection

Hydrogen sulfide ($H_2S$) is a colorless gas with the characteristic foul odor of rotten eggs; it is heavier than air, very poisonous, corrosive, flammable, and explosive. Interestingly the human body produces small amounts of $H_2S$ that acts as a signaling molecule and has gained increasing recognition as an important player in modulating acute and chronic inflammatory diseases. Its role in viral-induced infection is currently unknown. $H_2S$ can be provided or produced by donor molecules, i.e., molecules that undergo chemical changes that generate $H_2S$.

Hydrogen sulfide is produced in small amounts by some cells of the mammalian body and has a number of biological signaling functions. Only two other such gases are currently known: nitric oxide (NO) and carbon monoxide (CO). The gas is produced from cysteine by the enzymes cystathionine beta-synthase and cystathionine gamma-lyase. $H_2S$ acts as a relaxant of smooth muscle and as a vasodilator. $H_2S$ is also active in the brain where it increases the response of the NMDA receptor and facilitates long-term potentiation, which is involved in the formation of memory. Eventually $H_2S$ is converted to sulfite in the mitochondria by thiosulfate reductase, and the sulfite is further oxidized to thiosulfate and sulfate by sulfite oxidase. The sulfates are excreted in the urine.

Due to effects similar to nitric oxide (without its potential to form peroxides by interacting with superoxide), hydrogen sulfide is now recognized as potentially protective against cardiovascular disease. Though both nitric oxide (NO) and hydrogen sulfide have been shown to relax blood vessels, their mechanisms of action are different: while NO activates the enzyme guanylyl cyclase, $H_2S$ activates ATP-sensitive potassium channels in smooth muscle cells.

Hydrogen sulfide donors include, but are not limited to G 4137 ((p-methoxyphenyl)morpholino-phosphinodithioic acid); NaHs; ACS67 (7-[(1R,2R,3R,5S)-3,5-dihydroxy-2-[(3R)-3-hydroxy-5-phenylpentyl]cyclopentyl]-4-(3-thioxo-3H-1,2-dithiol-5-yl)phenyl ester, 5Z-heptenoic acid); diallyl trisulfide (di-2-propen-1-yl trisulfide); ATB-343 (1-(4-chlorobenzoyl)-5-methoxy-2-methyl-4-(3-thioxo-3H-1,2-dithiol-5-yl)phenyl ester-1H-indole-3-acetic acid); ATB-337 (4-(3-thioxo-3H-1,2-dithiol-5-yl)phenyl ester-2-[(2,6-dichlorophenyl)amino]-benzeneacetic acid), and AP67 (pyrrolidinium 4-methoxyphenyl(pyrrolidin-1-yl)phosphinodithioate).

$H_2S$ donors differ in their $H_2S$ release kinetics with some donors being classified as fast release (e.g., NaHS) and other being classified as slow-release (e.g, Gyy4137). Slow-releasing $H_2S$ donors have a half-life of at least 1 minute to 80 minutes or longer under physiologic conditions. Fast release $H_2S$ donors have a half-life of less than one minute under physiologic conditions.

III. Formulations and Administration

One non-limiting benefit of embodiments described herein is that therapeutic compositions can be delivered and have effect quickly and easily. The disclosed compositions can be formulated as pharmaceutical compositions for the administration to a subject. Pharmaceutical compositions may be administered via the respiratory system of a subject. In certain aspects the compositions are deposited in the lung by methods and devices known in the art. Compositions may be prepared in water suitably mixed with a surfactant, such as hydroxypropylcellulose. Dispersions may also be prepared in glycerol, liquid polyethylene glycols and mixtures thereof, and in oils. Under ordinary conditions of storage and use, these preparations contain a preservative to prevent the growth of microorganisms. The pharmaceutical forms suitable for inhalation include sterile aqueous solutions or dispersions and sterile powders for the extemporaneous preparation of sterile inhalable solutions or dispersions. In all cases the form is typically sterile and capable of inhalation directly or through some intermediary process or device. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. The prevention of the action of microorganisms can be brought about by various antibacterial and antifungal agents, for example, parabens, chlorobutanol, phenol, sorbic acid, thimerosal, and the like.

Some variation in dosage will necessarily occur depending on the condition of the subject being treated and the particular circumstances involving exposure or potential exposure. The person responsible for administration will, in any event, determine the appropriate dose for the individual subject. Moreover, for human administration, preparations should meet sterility, pyrogenicity, general safety, and purity standards as required by FDA Office of Biologics standards or other similar organizations.

Sterile compositions are prepared by incorporating the active components in the required amount in the appropriate solvent with various other ingredients enumerated above, as required, followed by, for example, filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile compositions, some methods of preparation are vacuum-drying and freeze-drying techniques which yield a powder of the active ingredient plus any additional desired ingredient from a previously sterile-filtered solution.

Pulmonary/respiratory drug delivery can be implemented by different approaches, including liquid nebulizers, aerosol-based metered dose inhalers (MDI's), sprayers, dry powder dispersion devices and the like. Such methods and compositions are well known to those of skill in the art, as indicated by U.S. Pat. Nos. 6,797,258, 6,794,357, 6,737,045, and 6,488,953, all of which are incorporated by reference. According to some embodiments, at least one pharmaceutical composition can be delivered by any of a variety of inhalation or nasal devices known in the art for administration of a therapeutic agent by inhalation. Other devices suitable for directing pulmonary or nasal administration are also known in the art. Typically, for pulmonary administration, at least one pharmaceutical composition is delivered in a particle size effective for reaching the lower airways of the lung or sinuses. Some specific examples of commercially available inhalation devices suitable for the practice of methods are Turbohaler™ (Astra), Rotahaler® (Glaxo), Diskus® (Glaxo), Spiros™ inhaler (Dura), devices marketed by Inhale Therapeutics, AERx™ (Aradigm), the Ultravent® nebulizer (Mallinckrodt), the Acorn II® nebulizer (Marquest Medical Products), the Ventolin® metered dose inhaler (Glaxo), the Spinhaler® powder inhaler (Fisons), or the like.

All such inhalation devices can be used for the administration of a pharmaceutical composition in an aerosol. Such aerosols may comprise either solutions (both aqueous and non-aqueous) or solid particles. Metered dose inhalers typically use a propellant gas and require actuation during inspiration. See, e.g., WO 98/35888; WO 94/16970. Dry powder inhalers use breath-actuation of a mixed powder. See U.S. Pat. Nos. 5,458,135; 4,668,218; PCT publications WO 97/25086; WO 94/08552; WO 94/06498; and European application EP 0237507, each of which is incorporated herein by reference in their entirety. Nebulizers produce aerosols from solutions, while metered dose inhalers, dry powder inhalers, and the like generate small particle aerosols. Suitable formulations for administration include, but are not limited to nasal spray or nasal drops, and may include aqueous or oily solutions of a $H_2S$ composition.

A spray comprising a pharmaceutical composition can be produced by forcing a suspension or solution of a composition through a nozzle under pressure. The nozzle size and configuration, the applied pressure, and the liquid feed rate can be chosen to achieve the desired output and particle size. An electrospray can be produced, for example, by an electric field in connection with a capillary or nozzle feed.

A pharmaceutical composition can be administered by a nebulizer such as a jet nebulizer or an ultrasonic nebulizer. Typically, in a jet nebulizer, a compressed air source is used to create a high-velocity air jet through an orifice. As the gas expands beyond the nozzle, a low-pressure region is created, which draws a composition through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the composition creating an aerosol.

In a metered dose inhaler (MDI), a propellant, a composition, and any excipients or other additives are contained in a canister as a mixture with a compressed gas. Actuation of the metering valve releases the mixture as an aerosol.

Pharmaceutical compositions for use with a metered-dose inhaler device will generally include a finely divided powder containing a composition described herein as a suspension in a non-aqueous medium, for example, suspended in a propellant with the aid of a surfactant. The propellant can be any conventional material employed for this purpose such as chlorofluorocarbon, a hydrochlorofluorocarbon, a hydrofluorocarbon, or a hydrocarbon including trichlorofluoromethane, dichlorodifluoromethane, dichlorotetrafluoroethanol and 1,1,1,2-tetrafluoroethane, HFA-134a (hydrofluroalkane-134a), HFA-227 (hydrofluroalkane-227), or the like.

Methods may involve administering to the patient or subject at least or at most 1, 2, 3, 4, 5, 6, 7, 8, 9, 10 or more doses of a therapeutic composition. A dose may be a composition comprising about, at least about, or at most about 0.01, 0.05, 0.1, 0.5, 1.0, 5.0, 10.0, 15.0, 20.0, 50, 100, 200, 300, 400, 500, 600, 700, 800, 900, 1000 milligrams (mg) or micrograms (mcg) or µg/ml or micrograms/ml or mM or µM (or any range derivable therein) of $H_2S$ donor(s) or the total amount of a combination of $H_2S$ donors.

A dose may be administered on an as needed basis or every 1, 2, 3, 4, 5, 6, 7, 8, 9, 10, 11, 12, 18, or 24 hours (or any range derivable therein) or 1, 2, 3, 4, 5, 6, 7, 8, 9, or times per day (or any range derivable therein). A dose may be first administered before or after signs of an infection are exhibited or felt by a patient or after a clinician evaluates the patient for an infection. In some embodiments, the patient is administered a first dose of a regimen 1, 2, 3, 4, 5, 6, 7, 8, 9, 10, 11, 12 hours (or any range derivable therein) or 1, 2, 3, 4, or 5 days after the patient experiences or exhibits signs or symptoms of an infection (or any range derivable therein). The patient may be treated for 1, 2, 3, 4, 5, 6, 7, 8, 9, 10 or more days (or any range derivable therein) or until symptoms of an infection have disappeared or been reduced or after 6, 12, 18, or 24 hours or 1, 2, 3, 4, or 5 days after symptoms of an infection have disappeared or been reduced.

In compositions comprising two $H_2S$ donors, the ratio of the two $H_2S$ donors (e.g., fast release to slow release, or slow release to fast release) may be about 1:1, 2:1, 3:1, 4:1, 5:1, 6:1, 7:1, 8:1, 9:1, 10:1, 11:1, 12:1, 13:1, 14:1, 15:1, 20:1, 30;1, 40:1, 50:1, 60:1, 70:1, 80:1, 90:1, 100:1 or more, or any range derivable therein. In specific embodiments, the $H_2S$ donors can be Gyy4137, ACS67, NaHS, diallyl trisulfide, ATB-343, and/or ATB-337.

Treatment with a nebulizer may be at least or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, or 120 minutes in length (or any value or range there between). The nebulizer reservoir may contain a solution that comprises about, at least about or at most about 0.1, 1, 10, 50, 100, 150, 200, 250, 300, 400, 500, 600, 700, 800, 900, 1000 µg/ml or mg/ml (or any value or range there between) of each $H_2S$ donor or the total amount of a combination of $H_2S$ donors.

The volume that is administered in each dose may be about, at least about, or at most about 0.01, 0.05, 0.1, 1.0, 2.0, 3.0, 4.0, 5.0, 6.0, 7.0, 8.0, 9.0, 10.0, 15.0, 20.0 µl or ml (or any value or range there between).

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" refers to molecular entities and compositions that do not produce an allergic or similar untoward reaction when administered to a subject.

IV. Examples

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Herein is disclosed that treatment of target cells with $H_2S$ donors, such as slow release donor GYY4137, significantly reduced in vitro replication of several Group 5 viruses including viruses causing respiratory infection and Ebola. Further, treatment of RVFV has also been determined (not shown). The results indicate that $H_2S$ donors have a broad antiviral activity, spanning different unrelated families of highly pathogenic RNA viruses.

Example 1

Role of the Novel Gaseous Mediator Hydrogen Sulfide in the Pathophysiology of Paramyxovirus Infections A. Results RSV Infection Affects $H_2S$ Generation in Airway Epithelial Cells.

Figure 1D:
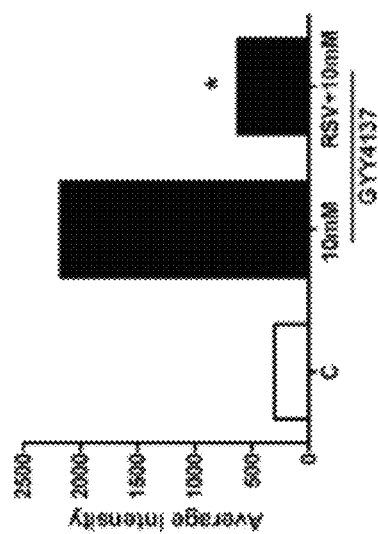
Figure 1D:
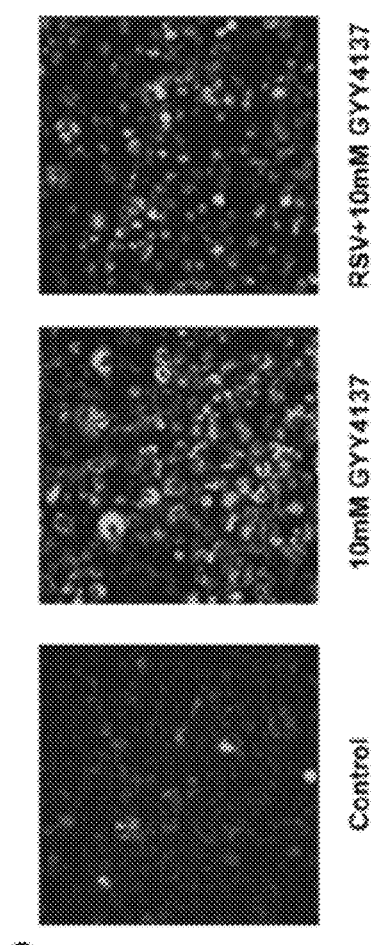

Of the three $H_2S$-generating enzymes CSE, CBS, and MST, CSE represents the major source of $H_2S$ in lung tissue, and it uses cysteine as the main substrate. Sulfide:quinone oxidoreductase (SQOR) is a membrane-bound enzyme that catalyzes the first step in the mitochondrial metabolism of $H_2S$ (Jackson et al., 2012, Biochemistry 51:6804-15). To determine whether RSV induced changes in $H_2S$-generating and -metabolizing enzymes in AECs, A549 cells were infected for 6, 15, and 24 h and harvested for extraction of total RNA and measurement of CSE, CBS, and SQOR mRNA levels by real-time PCR. We found that CSE mRNA and protein expression levels were decreased by RSV infection only at later time points (FIG. 1A), while there was no significant change in the CBS mRNA level (data not shown). On the other hand, there was a significant time-dependent increase in the SQOR mRNA expression level in RSV-infected cells compared to uninfected cells (FIG. 1C). To investigate whether RSV modulated the capacity of airway epithelial cells to generate $H_2S$, A549 cells were infected for 15 h and harvested to prepare total cell lysates. $H_2S$ production was then measured by a methylene blue assay. There was a significant reduction in $H_2S$ generation in RSV-infected cells, compared to uninfected cells, when cysteine was supplied at 1 and 3 mM concentrations as the CSE substrate (FIG. 1B). When A549 cells were treated with the slow-releasing $H_2S$ donor GYY4137, there was a significant increase in the intracellular level of $H_2S$ detected by the fluorescent probe SF7-AM, which was significantly lower in infected cells, suggesting an increase in $H_2S$ degradation following RSV infection (FIG. 1D).

CSE Inhibition Enhances RSV-Induced Chemokine Production and Viral Replication.

Figure 2A:
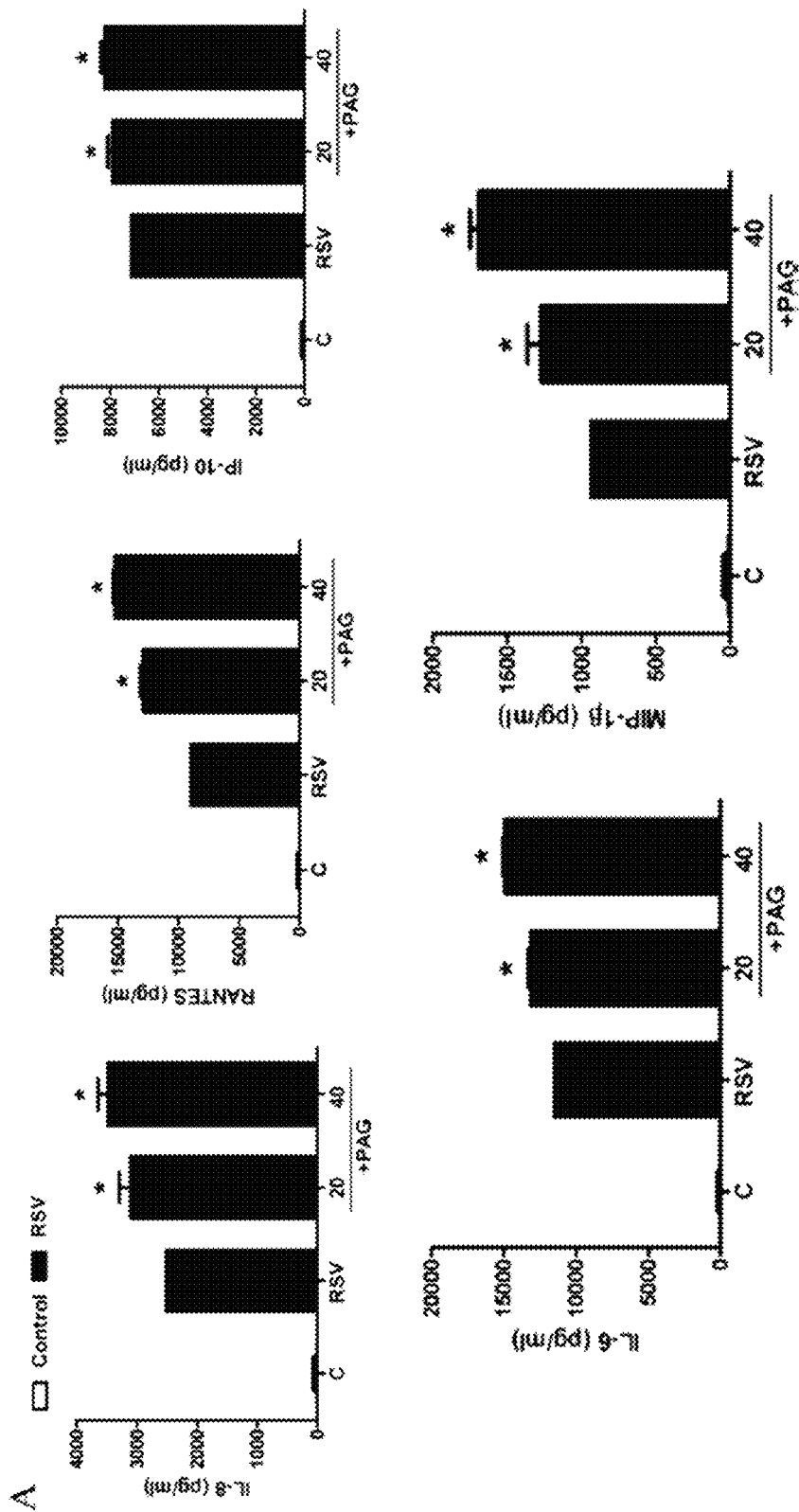
FIG. 2A-2B. Effect of CSE inhibition on RSV-induced cytokine and chemokine production and viral replication. A549 cells were infected with RSV for 1 h and then incubated in the presence or absence of 20 or 40 mM PAG. (A) Cell supernatants from uninfected and RSV-infected cells, treated or untreated, were assayed at 24 h p.i. for cytokine and chemokine secretion by a Bio-Plex assay. Results are expressed as means standard errors. Results are representative of data from three independent experiments run in triplicate. (B) Cells were treated as described above for panel A and harvested at 24 h p.i. to determine viral titers by a plaque assay. *, P<0.05 compared to untreated RSV-infected cells.
Figure 2B:
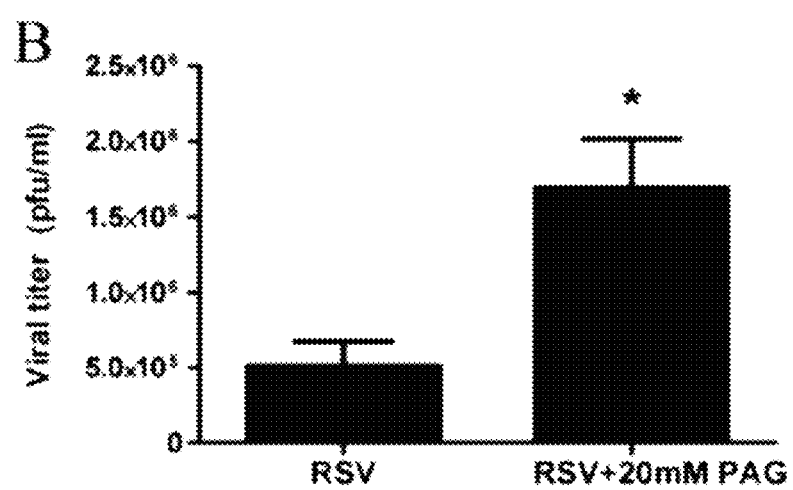

To examine the effect of CSE inhibition on virus-induced cellular responses, A549 cells were infected with RSV for 1 h and then treated with different concentrations of DL-propargylglycin (PAG). Cell supernatants were harvested at 24 h p.i. to measure virus-induced chemokine secretion. PAG administration significantly increased the levels of production of several cytokines and chemokines in response to RSV infection in a dose-dependent manner (FIG. 2A). PAG treatment of A549 cells also resulted in a significant increase in viral infectious-particle formation (3- to 4-fold increase), assessed by a plaque assay (FIG. 2B), indicating a role of endogenous $H_2S$ production in viral replication and proinflammatory cellular responses.

Effect of $H_2S$ Treatment on RSV-Induced Proinflammatory Mediator Production.

Figures 3A, 3B:
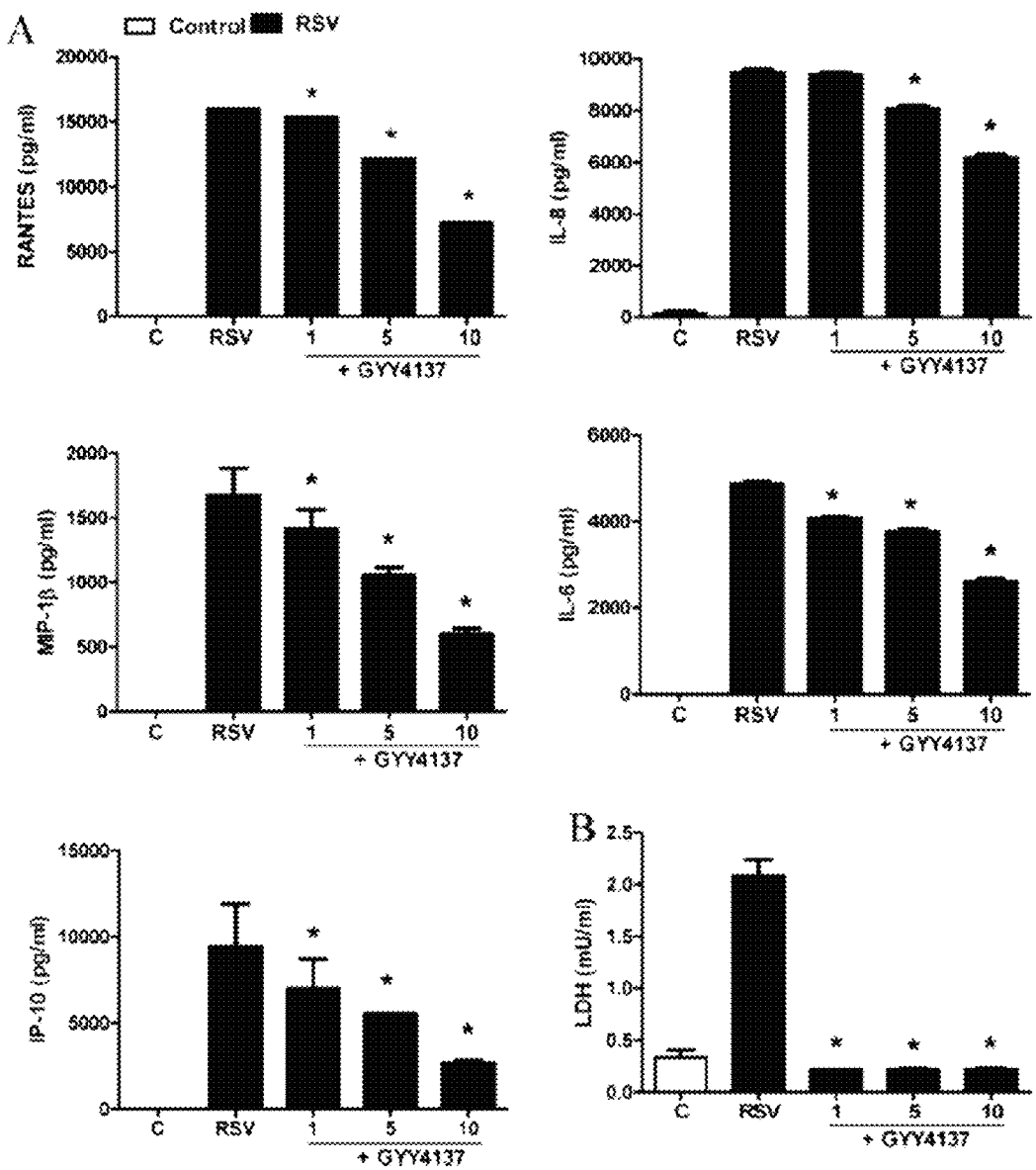
FIG. 3A-3B. Effect of $H_2S$ donor treatment on RSV-induced cytokine and chemokine production in A549 cells. Cells were infected with RSV for 1 h and then incubated in the presence or absence of GYY4137 at 1, 5, and 10 mM for 24 h. Cell supernatants were assayed for cytokine and chemokine secretion by an ELISA or a Bio-Plex assay (A) and for cytotoxicity by an LDH release assay (B). Results are expressed as means±standard errors and are representative of data from at least three independent experiments run in triplicate for the experiments described above for panel A. *, P<0.05 compared to untreated RSV-infected cells.
Figure 4:
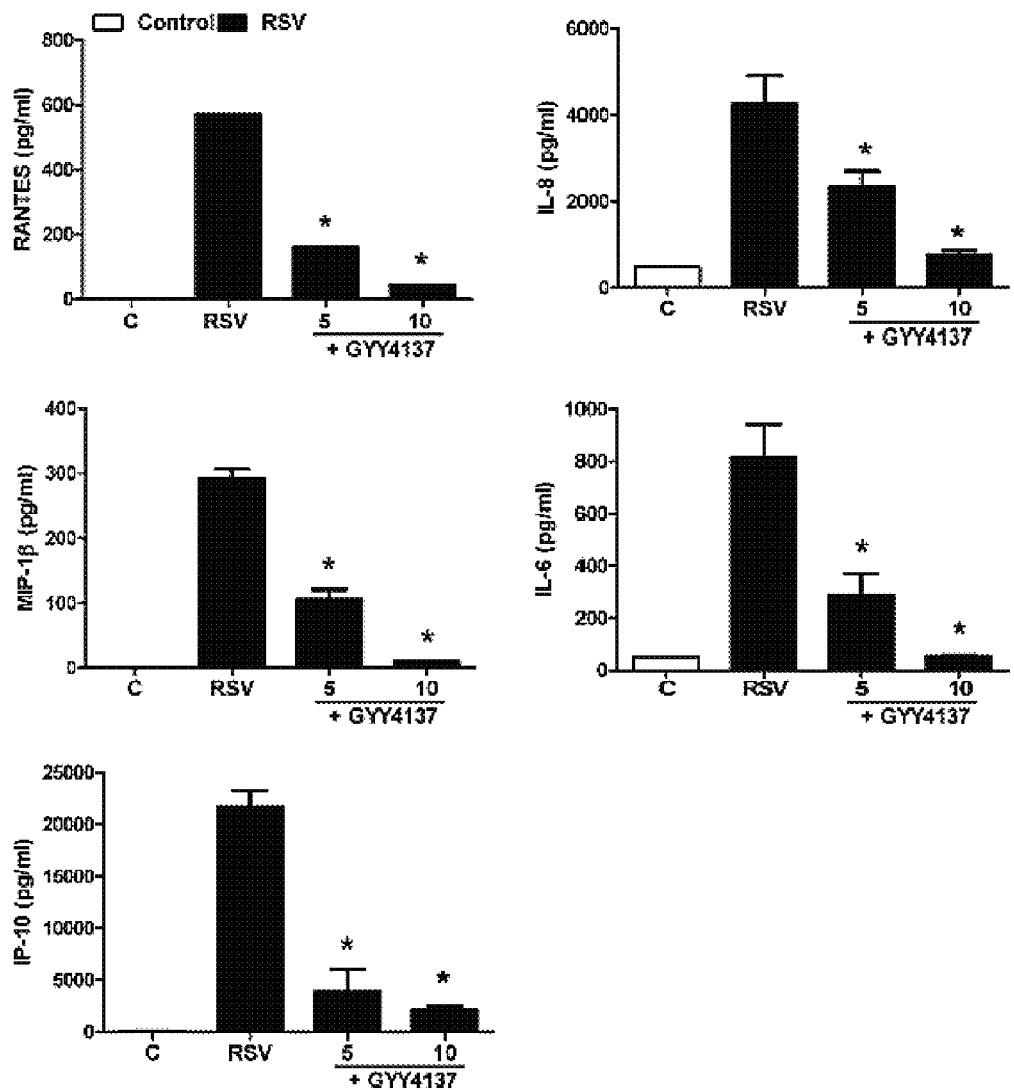
FIG. 4. Effect of $H_2S$ donor treatment on RSV-induced cytokine and chemokine production in SAE cells. Cells were infected with RSV for 1 h and then incubated in the presence or absence of GYY4137 at 5 and 10 mM for 24 h. Cell supernatants were assayed for cytokine and chemokine secretion by an ELISA or a Bio-Plex assay. Results are expressed as means±standard errors and are representative of data from three independent experiments run in triplicate. *, P<0.05 compared to untreated RSV-infected cells.

To investigate the effect of increasing intracellular H2S levels on viral responses, we determined levels of cytokine and chemokine secretion in A549 cells infected with RSV in the presence or absence of GYY4137, a slow-releasing $H_2S$ donor. A549 cells were infected with RSV for 1 h, followed by incubation with different concentrations of GYY4137, and harvested to collect the cell supernatant at 24 h p.i. to measure proinflammatory mediator release by ELISAs and Bio-Plex assays. RSV-induced secretion of several cytokines and chemokines, such as IL-6, IL-8, RANTES, macrophage inflammatory protein 1β (MIP-1β), and interferon-induced protein 10, was decreased by GYY4137 treatment in a dose-dependent manner (FIG. 3A). To investigate possible GYY4137 cytotoxicity, supernatants of uninfected or infected and treated or untreated A549 cells were harvested and tested for LDH release. There was no enhanced cellular damage; on the contrary, we observed a protective effect against virus-induced cytotoxicity in response to GYY4137 treatment (FIG. 3B). Inhibition of proinflammatory secretion, following RSV infection, by GYY4137 administration was also confirmed in SAE cells, normal human AECs, which we have shown to behave very similarly to A549 cells in terms of chemokine/cytokine gene expression and transcription factor and signaling pathway activation in response to RSV infection (Bao et al., 2007, *Virology* 368:91-101; Olszewska-Pazdrak et al., 1998, *J Virol* 72:4756-64; Garofalo et al., 1996, *J Virol* 70:8773-81; Casola et al., 2001, *J Biol Chem* 276:19715-22; Zhang et al., 2001, *J Virol* 75:9044-58; Pazdrak et al., 2002, *Am J Physiol Lung Cell Mol Physiol* 283:L364-L372; Hosakote et al., 2011, *Am J Respir Crit Care Med* 183:1550-60) (FIG. 4).

Effects of $H_2S$ Treatment on RSV Replication.

Figure 5:
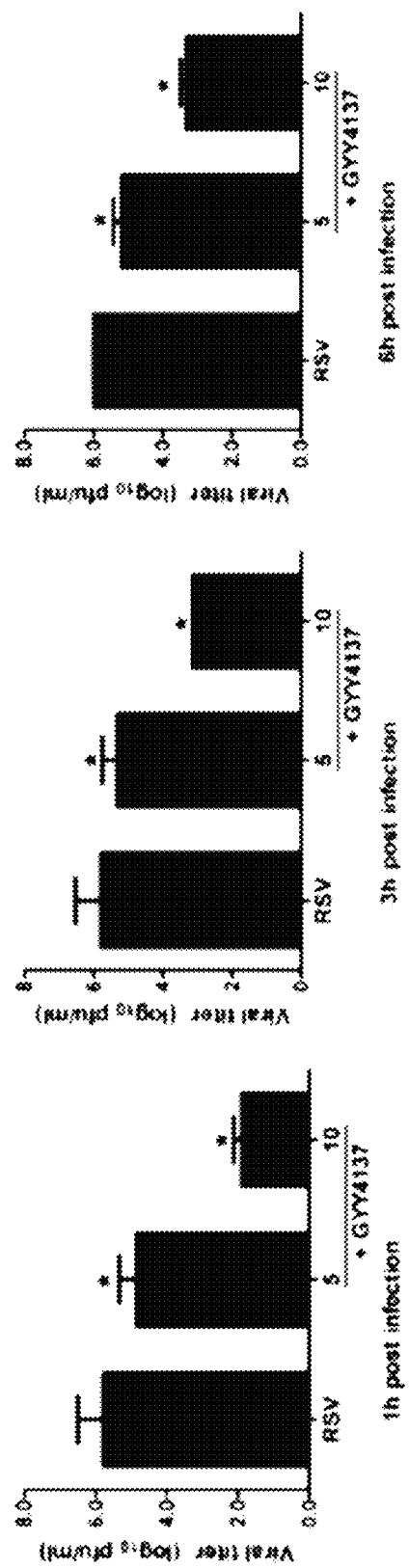
FIG. 5. Effect of $H_2S$ donor treatment on RSV replication. A549 cells were infected with RSV for 1, 3, or 6 h and then incubated in the presence or absence of GYY4137 at 5 and 10 mM for 24 h. Cells were harvested to determine viral titers by a plaque assay. Results are expressed as means±standard errors and are representative of data from five independent experiments run in triplicate. *, P<0.05 compared to untreated RSV-infected cells.

To determine whether increasing intracellular $H_2S$ levels affect viral replication, A549 cells were treated with different concentrations of GYY4137 either 1 h prior to RSV adsorption, until adsorption but not during infection, or 1 h after RSV adsorption and throughout infection and harvested at 24 p.i. to measure viral titers by a plaque assay. There was no change in viral titers when GYY4137 was given before infection (data not shown), while there was a significant decrease in RSV replication when GYY4137 was added after adsorption, in particular with the highest dose of the $H_2S$ donor, in the order of a several-log reduction (FIG. 5, left), indicating significant antiviral activity of $H_2S$ administration. To investigate whether this effect was reproducible if GYY4137 was administered several hours after infection, A549 cells were treated at 3 and 6 h p.i. and harvested to measure viral titers. We observed a significant decrease in RSV replication with both treatments, although the decrease was somewhat less striking than that with administration at 1 h p.i. (FIG. 5, middle and right), indicating that GYY4137 can affect viral replication when infection is already established.

$H_2S$ Treatment Affects Virus Particle Release and Syncytium Formation.

Figures 6A, 6B, 6C:
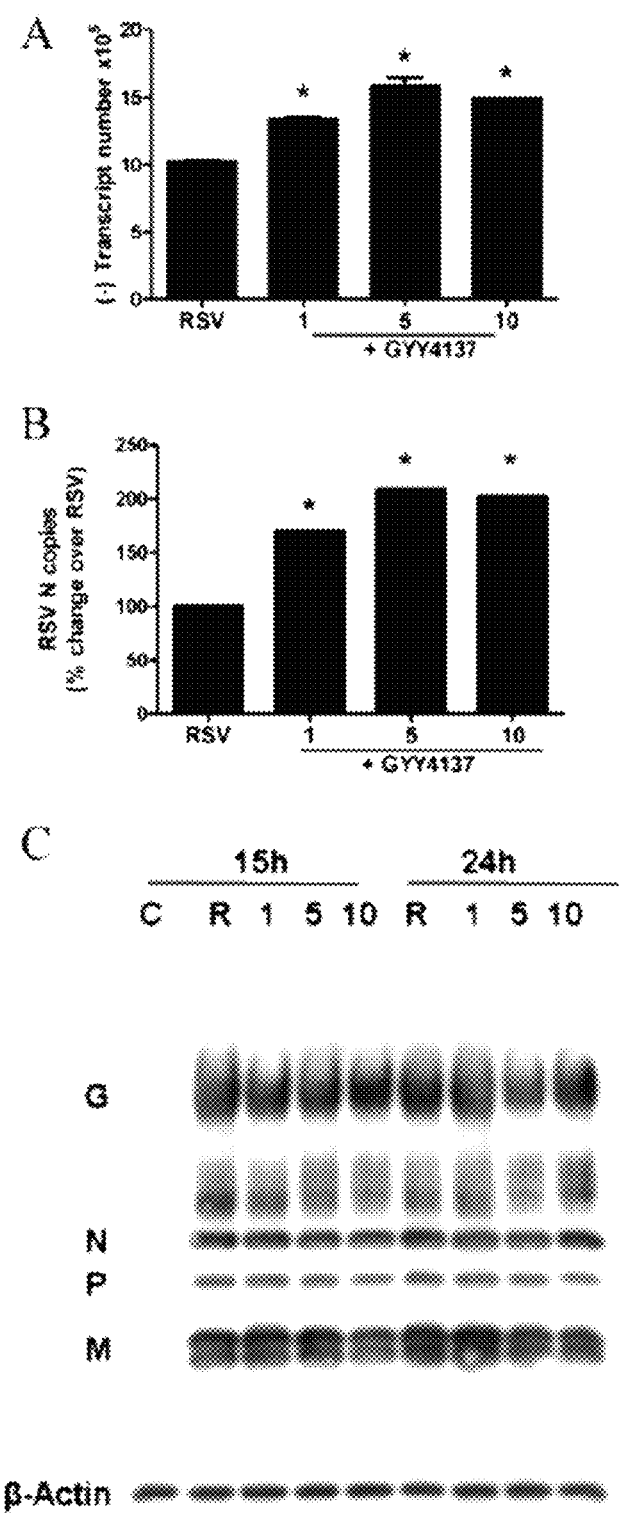
Figures 6F, 6G:
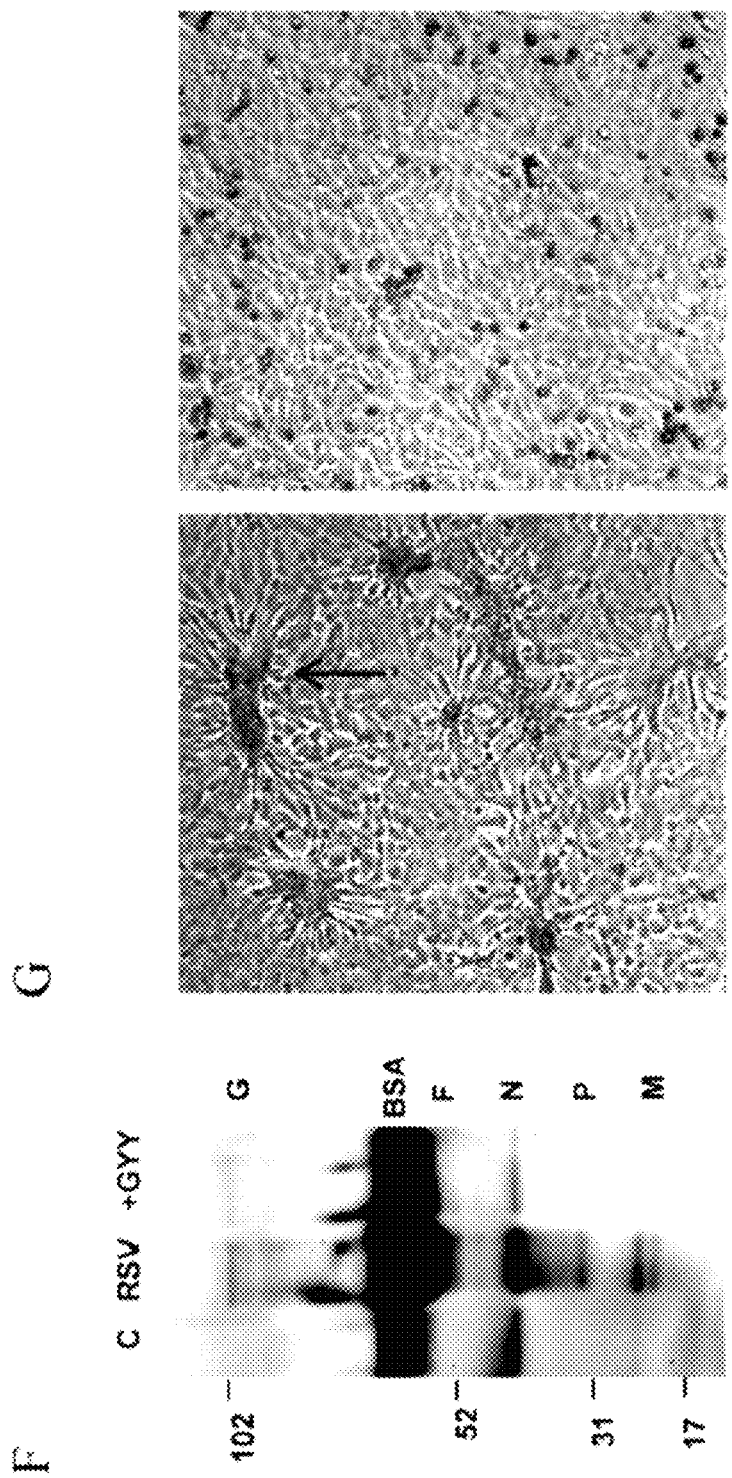

To further investigate how $H_2S$ treatment affected viral replication, we used several approaches, including quantification of viral gene transcription, genome replication, viral antigen detection, and viral particle release. GYY4137 administration did not decrease the number of RSV genome copies and N gene copies; on the contrary, they were somewhat increased at all concentrations tested (FIGS. 6A and 6B). Viral protein expression, assessed by a Western blot assay of total cell lysates, was not significantly affected by GYY4137 treatment at any of the doses tested (FIG. 6C). When viral titers were assessed separately on cell supernatants and cell pellets, we found that GYY4137 administration dramatically reduced the number of infectious virus particles present in the cell supernatant, with a much less robust effect on those associated with the cell pellet (FIG. 6D, left versus right), suggesting that $H_2S$ treatment affects viral replication in part at the level of virus assembly but mostly at the level of virus release. When viral replication was assessed in a multicycle replication system, this resulted in a significant inhibition of the cell-associated virus content in addition to the almost complete absence of virus in the cell supernatant of infected cells treated with the higher dose of GYY4173 (FIG. 6E). To determine whether the reduction in viral titers in cell supernatants was due to fewer virus particles released or to a loss of infectivity, we performed a Western blot analysis of viral proteins in supernatants from cells infected in the absence or presence of GYY4173. We found clear decreases in the levels of most of the viral proteins, with the exception of the G protein, which represents in good part a secreted protein (FIG. 6F). Moreover, we observed a striking reduction in cellular syncytium formation, suggesting that GYY4137 treatment can significantly affect virus-induced cellular fusion (FIG. 6G).

Effect of GYY4137 on RSV-Induced Cellular Signaling.

Cytokine and chemokine gene expression in A549 cells infected by RSV is orchestrated by the activation of the two key transcription factors NF-κB and IRF-3. To determine whether changes in RSV-induced cytokine and chemokine production observed with GYY4137 treatment affected NF-κB- and IRF-3-dependent gene transcription, we performed reporter gene assays. Cells were transiently transfected with either a NF-κB- or IRF-driven luciferase reporter plasmid and then treated with GYY4137 after 1 h of viral adsorption and harvested at 24 h p.i. to measure luciferase activity. RSV infection significantly enhanced both IRF-3- and NF-κB-dependent gene transcription, which was significantly inhibited by GYY4137 treatment in a dose-dependent manner (FIGS. 7A and 7B), consistent with the observed reduction in IL-8 and RANTES secretion.

Figures 7A, 7B, 7C, 7D, 7E:
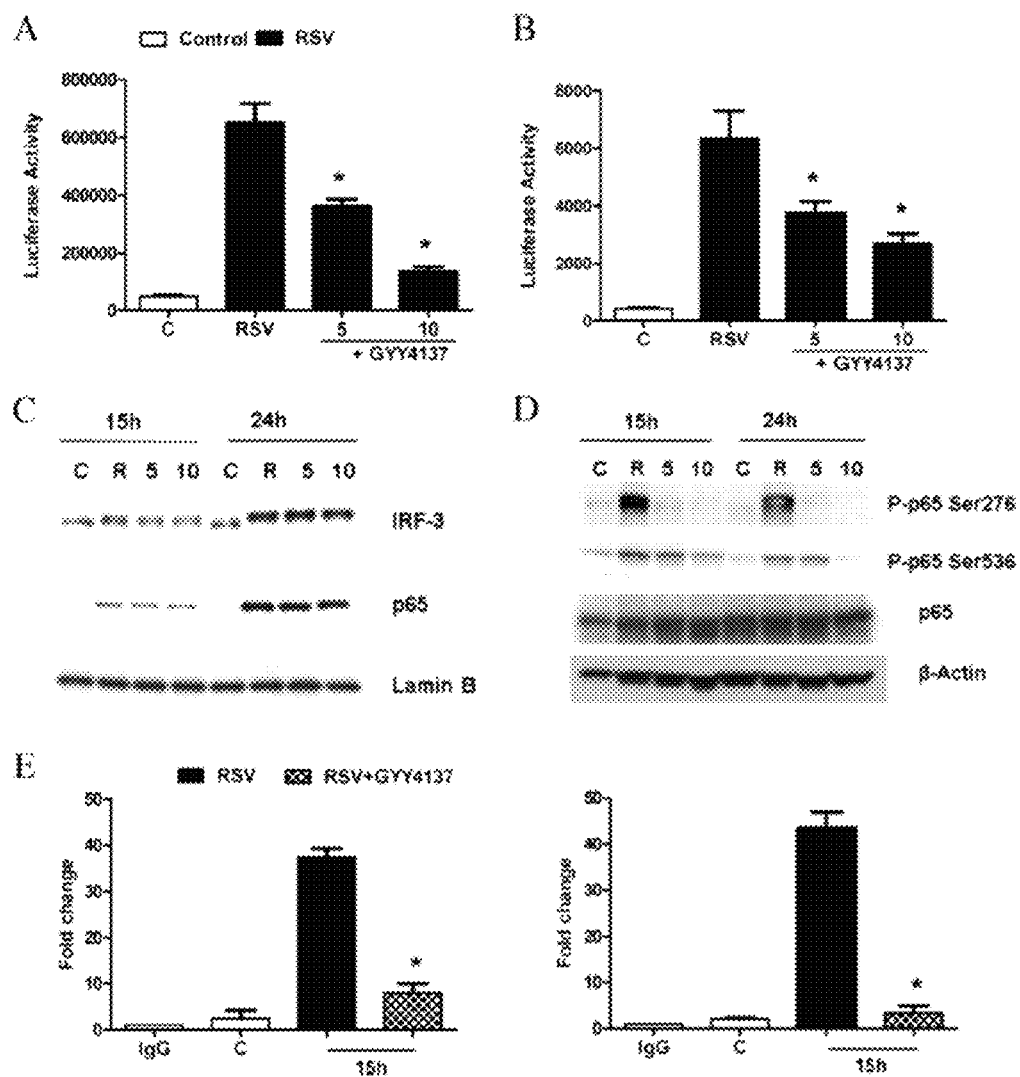
FIG. 7A-7E. Effect of $H_2S$ donor treatment on virus-induced signaling. (A and B) A549 cells were transiently transfected with an ISRE-driven (A) or NF-κB-driven (B) reporter gene plasmid, infected with RSV for 1 h, and then treated with 5 and 10 mM GYY4137. Cells were harvested at 15 or 24 h p.i. to measure luciferase and β-galactosidase reporter activities. Luciferase activity was normalized to the activity of the internal control β-galactosidase. Results are representative of data from three independent experiments run in triplicate. Data are expressed as means standard errors for normalized luciferase activity. *, P<0.05 relative to untreated, RSV-infected cells. (C) A549 cells were infected with RSV for 1 h, followed by GYY4137 treatment at different concentrations, and harvested at 15 and 24 h p.i. to prepare either total cell lysates or nuclear extracts. IRF-3 and p65 nuclear translocation was assessed by Western blotting of nuclear extracts. Membranes were stripped and reprobed with lamin B to determine equal loading of the samples. (D) Total Ser276 and Ser536 p65 phosphorylation levels were determined by Western blotting of total cell lysates. The membrane was stripped and reprobed for total p65 and β-actin to determine equal loading of the samples. Data are representative of data from three independent experiments with similar results. (E) Chromatin DNA from uninfected and RSV-infected A549 cells in the presence or absence of GYY4137 for 15 h was immunoprecipitated by using an anti-NF-κB antibody (left), an anti-IRF-3 antibody (right), or IgG as a negative control. Q-gPCR was performed by using primers spanning either the NF-κB-binding site of the IL-8 promoter or the ISRE-binding site of the RANTES promoter. Total input chromatin DNA for immunoprecipitation was included as positive control for Q-gPCR amplification. The fold change was calculated compared to the IgG control. Results are representative of data from two independent experiments. *, P<0.05 relative to untreated, RSV-infected cells.

To determine whether GYY4137 treatment was able to modulate virus-induced NF-κB and IRF-3 activation, A549 cells were infected with RSV for 1 h, incubated with or without GYY4137, and harvested at 15 and 24 h p.i. to prepare either total cell lysates or nuclear extracts. NF-κB and IRF-3 nuclear levels or cellular levels of phosphorylated serine in p65, the major NF-κB subunit activated in response to RSV infection (Garofalo et al., 1996, *J Virol* 70:8773-81), were assessed by Western blotting. Nuclear translocation of both transcription factors was not changed by GYY4137 treatment compared to RSV infection alone (FIG. 7C); however, there was a significant decrease in RSV-induced p65 Ser276 and Ser536 phosphorylation (FIG. 7D), two important posttranslational modifications that affect NF-κB transcriptional activity (Zhong et al., 1998, *Mol Cell* 1:661-71). In addition, GYY4137 treatment significantly reduced p65 and IRF occupancy of their cognate binding site on the IL-8 and RANTES endogenous promoters, assessed by a two-step chromatin immunoprecipitation (XChIP) and genomic PCR (Q-gPCR) assay (FIG. 7E). Taken together, these results indicate that increasing cellular $H_2S$ levels by using a slow-releasing donor can effectively modulate the strong proinflammatory cellular response induced by RSV infection through blocking IRF- and NF-κB-dependent gene transcription.

Effects of $H_2S$ Treatment on Chemokine Production and Viral Replication Induced by Other Paramyxoviruses.

Figures 8A, 8B:
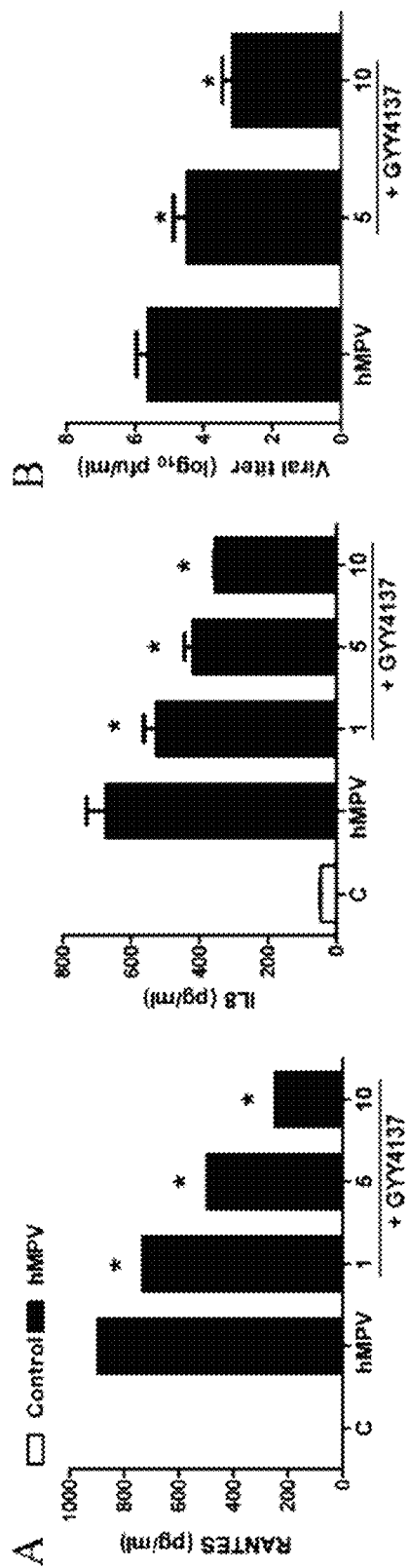
FIG. 8A-8B. Effect of $H_2S$ donor treatment on hMPV-induced chemokine production and viral replication. A549 cells were infected with hMPV for 1 h, followed by treatment with different millimolar concentrations of GYY4137. (A) Cell supernatants from uninfected and hMPV-infected cells, treated or untreated, were assayed at 24 h p.i. for cytokine and chemokine secretion by a Bio-Plex assay. Results are expressed as means±standard errors. Results are representative of data from two independent experiments run in triplicate. *, P<0.05 compared to untreated hMPV-infected cells. (B) Viral replication was determined at 24 h post-infection by titration of viral infectious particles released into the cell supernatants by a plaque assay. Results are representative of data from two independent experiments run in triplicate. *, P<0.05 compared to untreated hMPV-infected cells.
Figures 9A, 9B:
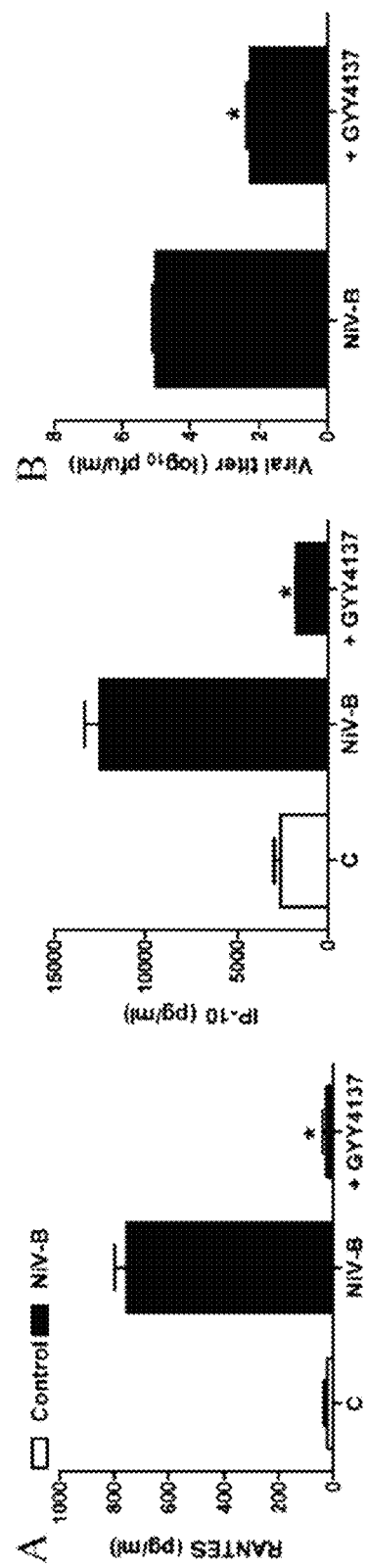
FIG. 9A-9B. Effect of $H_2S$ donor treatment on NiV-induced chemokine production and viral replication. SAE cells were infected with NiV at an MOI of 0.1 for 1 h, followed by treatment with a 5 mM concentration of GYY4137. (A) Cell supernatants from uninfected and NiV-infected cells, treated or untreated, were assayed at 24 h p.i. for cytokine and chemokine secretion by a Bio-Plex assay. Results are expressed as means±standard errors. Results are representative of data from two independent experiments run in triplicate. *, P<0.05 compared to untreated NiV-infected cells. (B) Viral replication was determined at 24 h post-infection by titration of viral infectious particles released into cell supernatants by a plaque assay. Results are representative of data from two independent experiments run in triplicate. *, P<0.05 compared to untreated NiV-infected cells.
Figure 10:
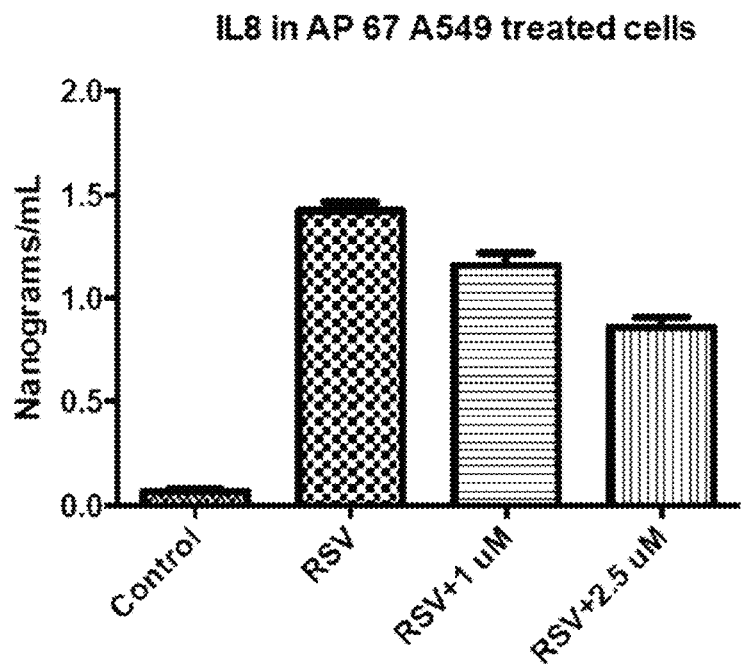
FIG. 10. Effect of AP67 treatment on RSV-induced IL-8 production in A549 treated cells.
Figure 11:
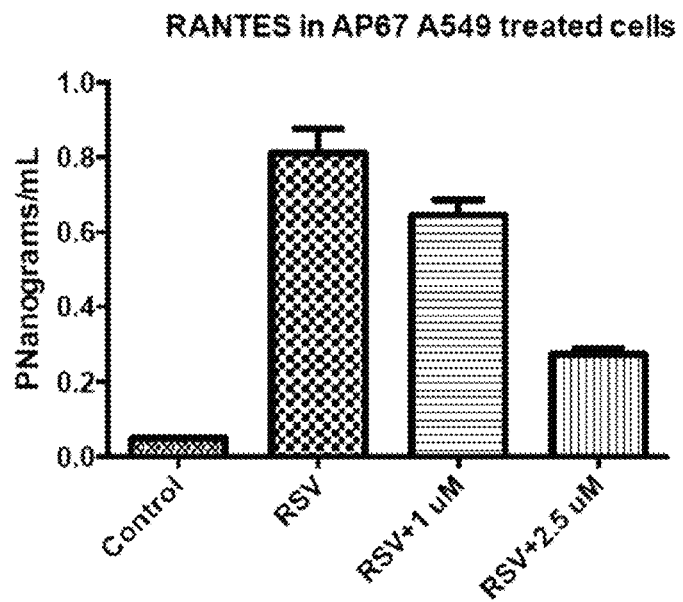
FIG. 11. Effect of AP67 treatment on RSV-induced RANTES production in A549 treated cells.

To investigate whether GYY4137 had similar antiviral and anti-inflammatory effects on other paramyxoviruses, we measured chemokine secretion and viral replication in A549 cells in response to hMPV infection. A549 cells were infected with hMPV for 1 h and incubated in the presence or absence of GYY4137 for a total of 24 h. Cell supernatants were collected to measure levels of IL-8 and RANTES induction by an ELISA, while viral titers were determined by immunostaining hMPV-induced IL-8 and RANTES secretion was significantly decreased by GYY4137 treatment in a dose-dependent manner (FIG. 8A). Similarly, viral replication was also significantly reduced by GYY4137 treatment (FIG. 8B). A similar experiment was conducted by using a model of SAE cells infected with NiV-B. Similarly to RSV and hMPV, GYY4137 treatment led to a significant reduction of virus-induced cytokine and chemokine secretion (FIG. 9A) and inhibition of viral replication (FIG. 9B). In addition, GYY4137 treatment inhibited syncytium formation in response to both hMPV and NiV infection (data not shown), suggesting that GYY4137 has a broad antiviral effect on paramyxoviruses.

B. Materials and Methods

Materials.

GYY4137 [morpholin-4-ium-4-methoxyphenyl(morpholino)phosphinodithioate], a novel water-soluble, slow-releasing $H_2S$ compound, and DL-propargylglycin (PAG), an inhibitor of the $H_2S$-generating enzyme cystathionine-γ-lyase (CSE), were purchased from Sigma-Aldrich (St. Louis, Mo., USA). Solutions were prepared freshly in culture medium and filtered through a 0.2-μm filter before treatment. Sulfidefluor-7-acetoxymethyl ester (SF7-AM), a fluorescent probe that allows direct, real-time visualization of endogenous $H_2S$ produced in live human cells (Lin et al., 2013, *Proc Natl Acad Sci USA* 110:7131-35), was generously provided by Christopher J. Chang (Department of Chemistry, University of California, Berkeley). An SF7-AM stock solution was prepared in dimethyl sulfoxide (DMSO) and diluted in serum-free medium at least a thousand-fold.

Virus Preparation.

The RSV Long strain was grown in HEp-2 cells and purified by centrifugation on discontinuous sucrose gradients, as described previously (Ueba, 1978, *Acta Med Okayama* 32:265-72; Olszewska-Pazdrak et al., 1998, *J Virol* 72:4756-64), and titers of viral pools in PFU/ml were determined by using a methylcellulose plaque assay, as described previously (Kisch and Johnson, 1963, *Proc Soc Exp Biol Med* 112:583-89). No contaminating cytokines or lipopolysaccharide (LPS), tested by the *Limulus* hemocyanin agglutination assay, was found in these virus preparations. Virus pools were aliquoted, quick-frozen on dry ice-alcohol, and stored at −80° C. until use.

hMPV strain CAN97-83 was obtained from the Centers for Disease Control and Prevention (CDC), Atlanta, Ga., with permission from Guy Boivin at the Research Center in Infectious Diseases, Regional Virology Laboratory, Laval University, Quebec City, Canada; propagated on LLCMK2 cells; and purified on sucrose cushions, as previously described (Kolli et al., 2011, *J Immunol* 187:47-54). Titers of virus pools in PFU/ml were determined by immunostaining, as previously described (Kolli et al., 2011, *J Immunol* 187:47-54).

The Nipah virus Bangladesh strain (NiV-B) was obtained from the Special Pathogens Branch of the Centers for Disease Control and Prevention (Atlanta, Ga.). The virus was propagated on Vero cells, as previously described (Escaffre et al., 2013, *J Virol* 87:3284-94). Titers of virus pools were determined by a 50% tissue culture infective dose ($TCID_{50}$) assay, as previously described (Escaffre et al., 2013, *J Virol* 87:3284-94). All infectious work with NiV was performed in a class II biological safety cabinet in a biosafety level 4 (BSL4) laboratory at the Galveston National Laboratory.

Cell Culture and Viral Infection.

A549 cells, a human alveolar type II-like epithelial cell line (American Type Culture Collection, Manassas, Va.), and small alveolar epithelial (SAE) cells (Clonetics, San Diego, Calif.), derived from terminal bronchioli of cadaveric donors, were grown in F12K medium and SAE cell growth medium, respectively, containing 10% (vol/vol) fetal bovine serum (FBS), 10 mM glutamine, 100 IU/ml penicillin, and 100 μg/ml streptomycin for F12K medium and 7.5 mg/ml bovine pituitary extract (BPE), 0.5 mg/ml hydrocortisone, 0.5 μg/ml human epidermal growth factor (hEGF), 0.5 mg/ml epinephrine, 10 mg/ml transferrin, 5 mg/ml insulin, 0.1 μg/ml retinoic acid, 0.5 μg/ml triiodothyronine, 50 mg/ml gentamicin, and 50 mg/ml bovine serum albumin (BSA) for SAE cell medium. When SAE cells were used for RSV infection, they were changed to basal medium, not supplemented with growth factors, 6 h prior to and throughout the experiment. Confluent cell monolayers were infected with RSV or hMPV at multiplicity of infection (MOI) of 1, as previously described (Garofalo et al., 1996, *J Virol* 70:8773-81), unless otherwise stated. NiV infection was performed at an MOI of 0.01 (Escaffre et al., 2013, *J Virol* 87:3284-94). For PAG experiments, cells were seeded into 6-well or 24-well plates, infected with RSV for 1 h at 37° C. in 5% $CO_2$, and then treated with PAG after the viral inoculum was removed. For GYY4137 experiments, cells were seeded into 6-well or 24-well plates and treated either prior to infection, but not throughout the duration of infection, or at different times postinfection (p.i.), after the viral inoculum was removed. There was no effect of either compound on uninfected-cell viability, as assessed by trypan blue exclusion, or on basal cellular mediator secretion.

Methylene Blue Assay.

$H_2S$ production was measured by use of a colorimetric methylene blue assay, as previously described (Asimakopoulou et al., 2013, *Br J Pharmacol* 169:922-32). Briefly, cells were homogenized, incubated at 37° C. for 5 min, and then cooled on ice for 10 min. L-Cysteine (1 and 3 mmol/liter) and pyridoxal 5-phosphate (2 mmol/liter) were added and incubated for 1 h at 37° C. Zinc acetate (1%) and 10% trichloroacetic acid solutions were used to terminate the reaction. After the addition of N,N-dimethylphenylendiamine sulfate and $FeCl_3$ for 15 min, the optical absorbance of the solutions was measured at 650 nm.

SF7-AM Fluorescence Assay.

A549 cells were grown in eight-well Lab-Tek II glass chamber slides (Thermo Scientific, Pittsburgh, Pa., USA) and incubated with 5 μM SF7-AM probe at 37° C. for 30 min. After washing with culture medium, A549 cells were infected with RSV and treated with GYY4137, as described above. Confocal fluorescence imaging studies were performed with a Zeiss 710 laser scanning microscope with a 20× water objective lens, with Zen 2009 software (Carl Zeiss). SF7-AM was excited by using a 488-nm argon laser, and emission was collected by using a Meta detector at wavelengths of between 500 and 650 nm. Cells were imaged at 37° C. with 5% $CO_2$ throughout the experiment. Image analysis was performed by using Metamorph software (Carl Zeiss), and fluorescence was quantified by using the mean pixel intensity after setting a common threshold for all images.

Luciferase Assay.

A549 cells were transiently transfected by using a NF-κB- or interferon-stimulated responsive element (ISRE)-driven luciferase reporter plasmid containing five repeats of the NF-κB site of the IgG promoter or three repeats of the RANTES ISRE promoter, respectively, linked to the luciferase reporter gene, using Fugene 6 (Roche Diagnostic Corp., Indianapolis, Ind.), as previously described (Casola et al., 2001, *J Virol* 75:6428-39; Casola et al., 2000, *J Immunol* 164:5944-51). A total of 0.5 μg of the reporter gene plasmid and 0.05 μg of β-galactosidase expression plasmid/well were premixed with Fugene 6 and added to the cells in regular medium. The next day, cells were infected with RSV for 1 h, followed by treatment with GYY4137, and harvested at either 15 or 24 h p.i. to independently measure luciferase and β-galactosidase reporter activities, as previously described (Casola et al., 2000, *J Immunol* 164:5944-51). Luciferase activity was normalized to the activity of the internal control β-galactosidase. Results are expressed in arbitrary units.

Determination of Lactate Dehydrogenase Activity.

Lactate dehydrogenase (LDH) activity in the medium, an index of cellular damage, was measured by a colorimetric assay using a commercially available kit (Cayman Chemical, MI, USA) according to the manufacturer's instructions.

Quantitative Real-Time PCR.

Total RNA was extracted by using a ToTALLYRNAkit (catalog number AM1910; Ambion, Austin, Tex.). RNA samples were quantified by using a NanoDrop spectrophotometer (Thermo Fisher Scientific Inc., Wilmington, Del.), and quality was analyzed on an RNA Nano or Pico chip by using the Agilent 2100 bioanalyzer (Agilent Technologies). Synthesis of cDNA was performed with 1 μg of total RNA in a 20-μl reaction mixture by using the TaqMan Reverse Transcription Reagents kit from ABI (catalog number N8080234; Applied Biosystems). The reaction conditions were as follows: 25° C. for 10 min, 48° C. for 30 min, and 95° C. for 5 min. Quantitative real-time PCR amplification (performed in triplicate) was done with 1 μl of cDNA in a total volume of 25 μl by using Faststart Universal SYBR green master mix (catalog number 04913850001; Roche Applied Science). The final concentration of the primers was 300 nM. 18S RNA was used as a housekeeping gene for normalization. PCR assays were run with the ABI Prism 7500 sequence detection system with the following conditions: 50° C. for 2 min, 95° C. for 10 min, and then 95° C. for 15 s and 60° C. for 1 min for 40 cycles. The RSV N-specific reverse transcriptase (RT) primer contained a tag sequence from the bacterial chloramphenicol resistance (Cm$^r$) gene to generate the cDNA, because of self-priming exhibited by RSV RNA. Duplicate cycle threshold ($C_T$) values were analyzed in Microsoft Excel by the comparative $C_T$ ($\Delta\Delta C_T$) method according to the manufacturer's instructions (Applied Biosystems). The amount of target ($2^{-\Delta\Delta C_T}$) was obtained by normalization to the endogenous reference (18S) sample. To detect RSV N transcripts, we used RT primer 5-CTGCGATGAGTGGCAGGCTTTTTTTTTTT-TAACTCAAAGCTC-3 (SEQ ID NO:1); the tag is underlined. For PCR assays, we used RSV tag reverse primer CTGCGATGAGTGGCAGGC (SEQ ID NO:2) and forward primer ACTACAGTGTATTAGACTTACAGCAGAAG (SEQ ID NO:3). To detect the genome minus strand, we used RSV N RT primer 5-CTGCGATGAGTGGCAG-GCACTACAGTGTATTAGACTTACAGCAGAAG-3 (SEQ ID NO:4). For PCR assays, we used RSV tag primer CTGCGATGAGTGGCAGGC (SEQ ID NO:2) and primer RSV P GCATCTTCTCCATGRAATTCAGG (SEQ ID NO:5).

Western Blotting.

Nuclear extracts of uninfected and infected cells were prepared by using hypotonic/nonionic detergent lysis, according to a protocol described previously by Schreiber et al. (1989, *Nucleic Acids Res* 17:6419). To prevent contamination with cytoplasmic proteins, isolated nuclei were purified by centrifugation through 1.7M sucrose buffer for 30 min at 12,000 rpm, before nuclear protein extraction, as previously described (Brasier et al., 2004, *J Virol* 78:11461-76). Total cell lysates were prepared from uninfected and infected A549 cells by the addition of ice-cold lysis buffer (50 mM Tris-HCl [pH 7.4], 150 mM NaCl, 1 mM EGTA, 0.25% sodium deoxycholate, 1 mM $Na_3VO_4$, 1 mM NaF, 1% Triton X-100, and 1 μg/ml of aprotinin, leupeptin, and pepstatin). After incubation on ice for 10 min, the lysates were collected, and detergent-insoluble materials were removed by centrifugation at 4° C. at 14,000×g. Proteins (10 to 20 μg per sample) were then boiled in 2× Laemmli buffer and resolved on SDS-PAGE gels. Proteins were transferred onto a Hybond polyvinylidene difluoride membrane (Amersham, Piscataway, N.J.), and nonspecific binding sites were blocked by immersing the membrane in Tris-buffered saline-Tween (TBST) containing 5% skim milk powder or 5% bovine serum albumin for 30 min. After a short wash in TBST, membranes were incubated with the primary antibody for 1 h at room temperature or overnight at 4° C., depending on the antibody used, followed by incubation with horseradish peroxidase (HRP)-conjugated secondary antibody (Sigma, St. Louis, Mo.), diluted 1:10,000 in TBST, for 30 min at room temperature. After washing, proteins were detected by using an enhanced chemiluminescence system (RPN 2016; Amersham, GEHealthcare, United Kingdom) and visualized by autoradiography. Antibodies used for Western blot assays were goat anti-RSV polyclonal antibody from Ab D SeroTec; rabbit anti-p65, anti-Ser536, or anti-Ser276 p65 from Cell Signaling Technology Inc., Danvers, Mass.; and rabbit anti-IRF-3 from Santa Cruz Biotechnology, Santa Cruz, Calif.

Bio-Plex Assay.

Cell-free supernatants were tested for multiple cytokines and chemokines by using the Bio-Plex Cytokine Human multiplex panel (Bio-Rad Laboratories, Hercules, Calif.), according to the manufacturer's instructions. Interleukin-8 (IL-8) and RANTES were also quantified by an enzyme-linked immunosorbent assay (ELISA) according to the manufacturer's protocol (DuoSet; R&D Systems, Minneapolis, Minn.). Prior to analysis, NiV samples were inactivated on dry ice by gamma radiation (5 megarads).

Chromatin Immunoprecipitation and Quantitative Genomic PCR.

For chromatin immunoprecipitation (ChIP) assays, we used a ChIP-It express kit from Active Motif (Carlsbad, Calif.) according to the manufacturer's instructions, with some modifications. Briefly, A549 cells in a 10-cm plate were washed three times with phosphate-buffered saline (PBS) and fixed with freshly prepared 2 mM disuccinimidyl glutarate (DSG) for 45 min at room temperature. After three washes with PBS, cells were fixed with freshly prepared formaldehyde for 10 min and neutralized with glycine for 5 min at room temperature. Cells were harvested and disrupted by using a Dounce homogenizer to isolate nuclei. Nuclei were sheared by sonication to obtain DNA fragments of 200 to 1,500 bp. Twenty micrograms of sheared chromatin was immunoprecipitated with 5 μg of ChIP-grade anti-NF-κB (catalog number sc-722X) or anti-IRF-3 (catalog number sc-369X) antibodies from Santa Cruz Biotechnology and magnetic beads conjugated with proteinG at 4° C. overnight. Immunoprecipitation with IgG antibody was used as a negative control. Chromatin was reverse cross-linked, eluted from magnetic beads, and purified by using a Qiagen PCR purification kit (Qiagen, USA). Quantitative genomic PCR (Q-gPCR) was done by SYBR green-based real-time PCR using primers spanning the IL-8 gene NF-κB promoter site (forward primer AGGTTTGCCCTGAGGGGATG (SEQ ID NO:6) and reverse primer GGAGTGCTCCGGTGGCTTTT (SEQ ID NO:7) or primers spanning the RANTES gene ISRE promoter site (forward primer AGCGGCTTCCTGCTCTCTGA (SEQ ID NO:8) and reverse primer CAGCTCAGGCTGGCCCTTTA (SEQ ID NO:9)). Total input chromatin DNA for immunoprecipitation was included as a positive control for PCR amplification.

Statistical Analysis.

Statistical analyses were performed with the InStat 3.05 Biostatistics package from GraphPad, San Diego, Calif. To ascertain differences between two groups, Student's t test was used, and if more than two groups were compared, one-way analysis of variance was performed, followed by Tukey's post hoc test. P values of <0.05 were considered statistically significant. When indicated, values of measurement are expressed as means standard errors of the means (SEM) in the figures.

Example 2

Hydrogen Sulfide ($H_2S$) Functions as an Antiviral Mediator Controls Airway Responsiveness and Inflammation in Respiratory Syncytial Virus (RSV) Infection $H_2S$ is generated endogenously in mammalian tissues through two cystathionine enzymes, cystathionine-γ-lyase (CSE) and cystathionine-β-synthetase (CBS). The objective of this study was to explore the role of $H_2S$ in an experimental model of respiratory syncytial virus (RSV) infection by examining clinical disease and viral-mediated airway hyperresponsiveness (AHR) in 10-11 week-old C57BL/6 mice genetically deficient in the CSE enzyme (CSE−/−), which have a defect in $H_2S$ generation. The results show that compared to RSV-infected WT mice, RSV-infected CSE−/− mice exhibited a significant increase in AHR to methacholine challenge (p<0.05), and surprisingly increased peak viral replication in the lung (p<0.005). To further test the role of $H_2S$ in the context of viral infection we treated groups of 10-11 week-old BALB/c mice with increasing concentrations of GYY4137, a slow-releasing $H_2S$ donor.

The results show that intranasal delivery of GYY4137 (at dose as low as 50 mg/kg) to RSV-inoculated mice markedly improved disease parameters (p<0.05) and reduced viral replication in the lungs compared to untreated controls. The protective effects of $H_2S$ were associated with significant reduction of viral-induced inflammatory cytokines, including IL-1α, IL-6, KC, GM-CSF, MCP-1, TNF-α, and RANTES. Overall these results indicate that $H_2S$ exerts a novel antiviral activity in the lung and controls airway responsiveness and inflammatory signals that affect cytokine production in response to a clinical relevant human pathogen.

A. Material and Methods

Animals.

Female BALB/c mice were purchased from Harlan (Houston, Tex.). C57BL/6J/129 mice wild type (WT) used in this work were purchased from Jackson Laboratories (Bar Harbor, Me.). CSE KO mice on C57BL/6J background were generously provided by Dr. Csaba Szabo (Department of Anesthesiology, UTMB. Galveston, Tex.). CSE KO mice were bred in the animal research facility at UTMB. CSE KO mice were viable and fertile. Both genders CSE KO mice and age-matched WT background were used. PCR genotyping of CSE KO mice was performed using a three-primer assay. The mRNA expression levels of three $H_2S$-producing enzymes (CSE, CBS and 3-MST) were also quantitatively analyzed by real-time PCR. Mice were sacrificed by an intraperitoneal injection of ketamine and xylazine and exsanguinated via the femoral vessels as previously reported.

$H_2S$ Donor.

GYY4137 (morpholin-4-ium 4 methoxyphenyl(morpholino)phosphinodithioate) was purchased from Cayman Chemical (Ann Arbor, Mich.). GYY4137 was freshly prepared daily in phosphate buffered saline prior to mice delivery.

RSV Preparation.

The RSV Long strain was grown in Hep-2 cells (American 7 Type Culture Collection, Manassas, Va.) and purified by centrifugation on discontinuous sucrose gradients. The virus titer of the purified RSV pools was 8-9 $\log_{10}$ plaque forming units (PFU)/mL using a methylcellulose plaque assay. Virus pools were aliquoted, quick-frozen on dry ice/alcohol and stored at −80° C. until used. UV-inactivated RSV was generated by exposing RSV to UV radiation (UVG-54 Entela, CA) 30 min.

Mice Infection Protocol.

Initial experiments were conducted to identify an appropriate route and dose of exogenous $H_2S$ donor administration, GYY4137, in BALB/c mice. The intranasal instillation route delivery and a dosage of 50 mg/kg body weight were selected for these studies. $H_2S$ was administered exogenously before (preventive) and after (therapeutic) RSV infection. Groups of BALB/c mice were treated with GYY4137 or control vehicle 1 h before, 6 h and 20 h after infection. Under light anesthesia, mice were infected intranasally (i.n.) with 50 µl of RSV diluted in phosphate-buffered saline (PBS, at dose $5 \times 10^6$ PFU) or mock inoculated using the same volume of control buffer. In some experiments BALB/c mice were inoculated with either RSV dose $1 \times 10^6$ or $1 \times 10^5$ PFU. A total of four experimental groups consisting of two treatment groups, vehicle (PBS) and GYY4137, for each infection group, mock and RSV were used for all experiments.

Cystathionine γ-lyase (CSE) gene-deficient (CSE KO) mice were used as an additional approach to examine the role of endogenous $H_2S$ in the pathogenesis of RSV induced infection. Both genders CSE KO and WT age-matched mice were used. Control WT and CSE KO mice were inoculated i.n. with $10^7$ PFU of RSV, in a total volume of 50 µl, under light anesthesia. As mock treatment, all mice were inoculated with an equivalent volume of PBS.

Clinical Disease.

Animals from all groups were evaluated on a daily basis for weight loss, illness score, and presence of any respiratory symptoms over the experimental period. The percentage of weight change was plotted over time. We used a well-established clinical illness scale for mice to establish the severity of infection (0—healthy; 1—barely ruffled fur; 2—ruffled fur but active; 3—ruffled fur and inactive; 4—ruffled fur, inactive, and hunched; 5—dead). These parameters have been shown to closely correlate with lung pathology in experimental paramyxovirus infection of mice.

Broncholaveolar Lavage (BAL).

The inflammatory cells infiltrating the airways were harvested by BAL via the trachea by flushing the lungs twice with 1 mL of ice-cold PBS. A total of 100 µl of this BAL fluid from each mouse was retained for cytospin analysis, and the rest was immediately centrifuged and stored at −80° C. until analysis. Total number of BAL cells was counted with a hemacytometer and viability was assessed by trypan blue. BAL differential cell counts were determined using morphogenic criteria under light microscopy of Protocol HEMA3 (Fisher Scientific) stained cytospin with a total count of 200 cells per slide.

Measurement of Cytokines, Chemokines and IFNs.

Levels of cytokines and chemokines in BAL fluid were determined with the Bio-Plex Pro Mouse Group I 23-plex panel (Bio-Rad Laboratories, Hercules, Calif.). The range of the sensitivity of the assays is 1.5 to 60,000 pg/ml. Production levels of IFN-α. and IFN-β in BAL samples from mice were determined by commercial enzyme-linked immunosorbent assays (ELISA), following the manufacturer's protocol (PBL, Piscataway, N.J.).

Pulmonary Histopathology.

Selected mice in each group were killed at day 7 post-infection, and the entire lung was perfused, removed, and fixed in 10% buffered formalin and embedded in paraffin. Multiple 4-µm longitudinal cross-sections were stained with hematoxylin and eosin (H&E). The slides were analyzed and scored for cellular inflammation under light microscopy by a board-certified pathologist. Two separate grading systems were used to assess the lung inflammation. The first grading system measured the percentage of abnormal perivascular spaces in the tissue sections. The second grading system assigned a 0-4 grade based on severity (0=normal, 4=severe pathologic changes), to four different parameters: perivasculitis, bronchiolitis, alveolitis, and necrosis. Ten (10) high power fields were examined for each slide, and average grades were compared between groups and analyzed to determine whether observed difference were statistically significant.

Lung Viral Replication.

Lungs were removed from infected animals at day 5 after RSV infection. Tissue samples were homogenized in 1 ml of Dulbecco's modified Eagle's medium and centrifuged twice at 14,000 rpm for 1 min at 4° C. Serial two-fold dilutions of the supernatant were determined by plaque assay on HEP-2 cells under methylcellulose overlay. Plaques were visualized 5 days later.

Pulmonary Function Testing.

Airway hyperresponsiveness (AHR) was assessed in unrestrained mice at different times after infection using whole-body barometric plethysmography (Buxco, Troy, N.Y.) to record enhanced pause (Penh). Penh has previously been validated in animal models of AHR and infection associated airway obstruction. Respiratory activity was recorded for 5 min, to establish baseline Penh values. Mice were subsequently exposed to increasing doses of nebulized methacholine (3.25, 6.25, 12.5, 25, and 50 mg/ml) for 2 min, and data were recorded for another 3 min.

Lung function was measured invasively on anesthetized mice using FlexiVent system (SCIREQ, Montreal, QC, Canada). Ventilation in mice was maintained at a rate of 150 breaths/minute, a tidal volume of 0.3 ml and a positive end expiratory pressure of 3 cm water. Baseline pulmonary mechanics and responses to aerosolized methacholine (0 to 50 mg/ml) were then obtained by using the forced-oscillation technique.

Statistical Analysis.

The data were evaluated using ANOVA and two-tailed unpaired Student's t-test for samples with unequal variances to determine significant difference between each set of two groups (GraphPad Prism 5.02; GraphPad Software, Inc., San Diego, Calif.). Results are expressed as mean±standard error of the mean for each experimental group unless otherwise stated. $p<0.05$ value was selected to indicate significance.

B. Results

GYY4137 Treatment Ameliorates Viral-Induced Disease and Pulmonary Function in Response to RSV Infection.

Studies were directed to antiviral and anti-inflammatory potential of GYY4137 (morpholin-4-ium 4 methoxyphenyl (morpholino)phosphinodithioate), a slow-releasing $H_2S$ donor, in BALB/c mice experimentally infected with RSV. Initial experiments were conducted to identify an appropriate route of exogenous $H_2S$ administration, GYY4137. A dose-response was also established using increasing doses of GYY4137 with range from 50 mg to 300 mg/kg body weight. The doses of GYY4137 tested were well tolerated by the mice, with no signs of toxicity (assessed by body weight loss or illness score). The intranasal instillation route delivery and a dose of 50 mg/kg GYY4137 were selected for these studies. GYY4137 was freshly prepared daily in phosphate buffered saline prior to mice delivery. $H_2S$ was administered exogenously before (preventive) and after (therapeutic) RSV infection. Groups of mice were treated with GYY4137 or control vehicle 1 h before, 6 h and 20 h after infection. Mice were either infected with either RSV at dose $5 \times 10^6$ PFU/mouse or PBS (mock infected). A total of four experimental groups consisting of two treatment groups, vehicle (PBS) and GYY4137, for each infection group, mock and RSV were used for all experiments. Groups of RSV-infected mice or mock-infected under the protocol mentioned above were either assessed daily for body weight loss and clinical illness score or sacrificed at different time points (days 1, 5, and 7) for determination of lung viral titer, lung cytokines and chemokines production, type I IFNs, and histological changes in the lungs.

Figures 12A, 12B, 12C, 12D:
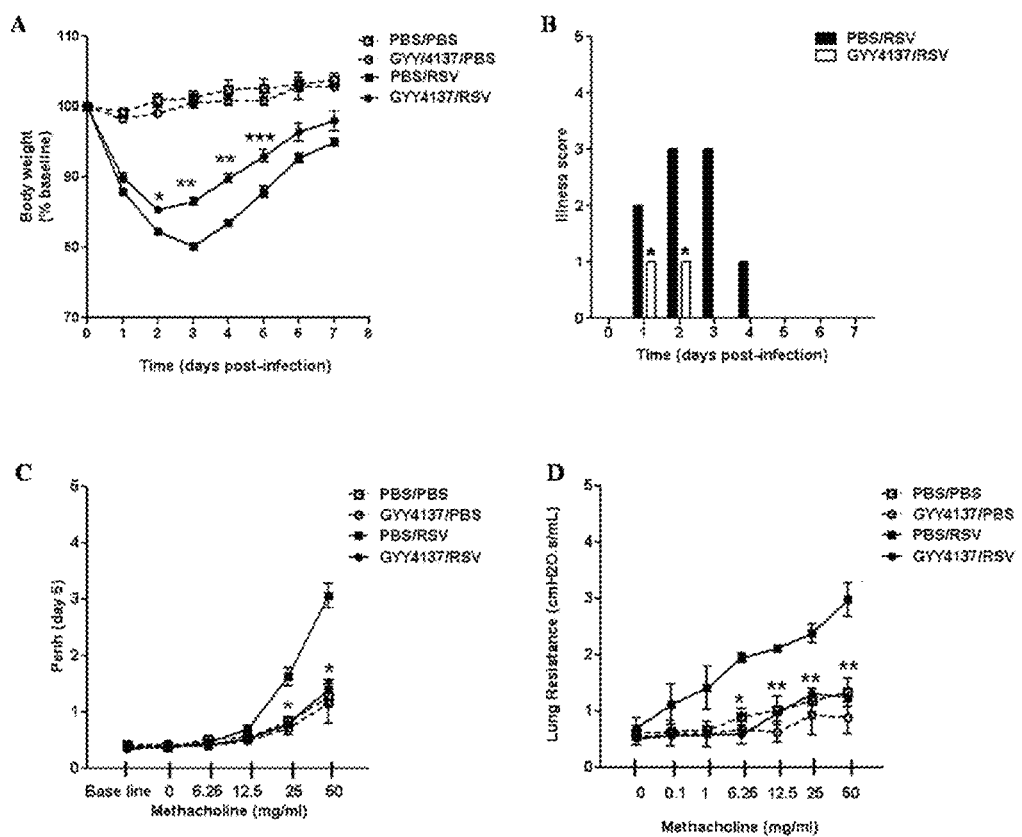
FIG. 12A-12D. GYY4137 treatment attenuates RSV-induced disease and pulmonary lung function. Mice were treated i.n. with GYY4137 (50 mg/kg body weight) or an appropriate volume of vehicle (PBS) 1 h before, 6 h and 20 h after infection. Mice were inoculated with either RSV or PBS, as described in Material and Methods. (A) Mice were monitored daily and body weight was calculated based on the original weight before the infection. Data are expressed as mean±SEM (n=4 mice/group). *$p<0.001$ compared with PBS/RSV at day 2 p.i., $p<0.0001$ compared with PBS/RSV at days 3, 4, and *$p<0.003$ compared with PBS/RSV at day 5 p.i. (B) Differences in the appearance of fur in RSV GYY4137—versus RSV vehicle-treated mice after infection. Clinical illness scores of GYY4137 RSV (open squares) and RSV vehicle (solid squares) were measured from day 1 to day 7 post-infection. Sham (mock) infected mice treated with either vehicle or GYY4137 received a healthy illness score 0 throughout the course of the experiment (data not shown). *$p<0.05$ compared with PBS/RSV. (C) Unrestrained, whole-body plethysmography (Buxco Electronics, Inc. Sharon, Conn.) was used to measure the Enhanced Pause (Penh) to evaluate AHR. Baseline and post-methacholine challenge Penh values were determined at day 5 after infection. Penh values are presented as mean±SEM (n=4-6 mice/group). *$p<0.0004$ compared with PBS/RSV. (D) Airway resistance (day 5 post-infection) measured in mechanically ventilated mice by the Flexivent system. Data are means±SEM (n=3 mice/group). *$p<0.0001$ compared with PBS/RSV, **$p<0.005$ compared with PBS/RSV group.

Weight loss is a clinical correlate of RSV infection therefore to determine whether GYY4137 treatment was capable of altering RSV-induced disease, body weights were measured up to day 7 after infection. As shown in FIG. 12A, mice inoculated with RSV alone progressively lost weight during the first 3 days of infection, with a peak of 20% loss at day 3 after infection. However, the 50 mg/kg dose of GYY4137 significantly attenuated RSV-induced body weight loss, as the mice experienced a weight loss of 15% at day 2 after infection. Furthermore, GYY4137 treated RSV-infected mice regained their original body weight earlier versus vehicle RSV-infected animals. No differences in weight loss or gain were observed for GYY4137 or vehicle treated mock-infected animals. In addition, we observed a significant difference in appearance of GYY4137 treated versus vehicle RSV-infected mice (FIG. 12B), estimated by the total illness score, starting at day 1 after infection.

Figures 18A, 18B:
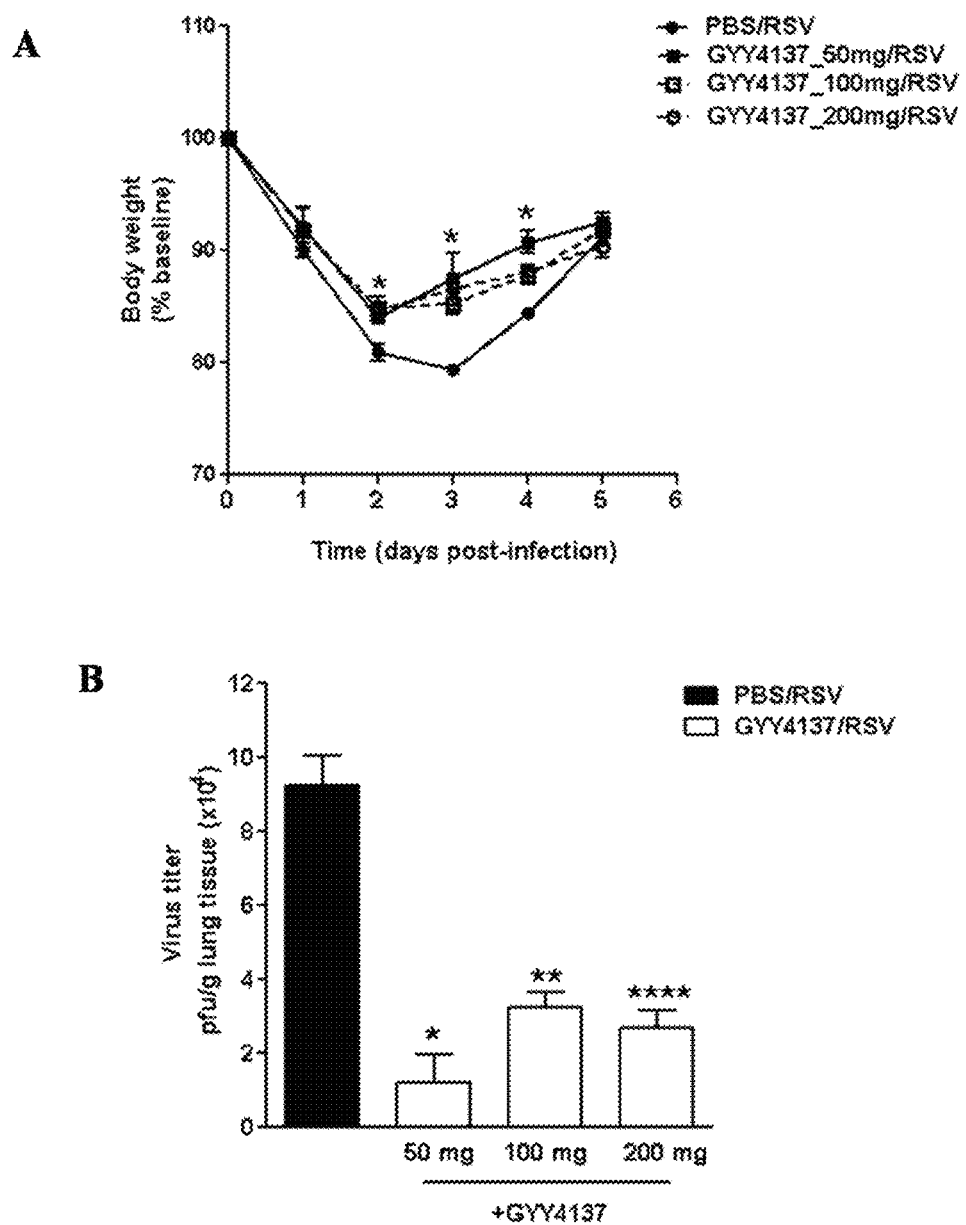
FIG. 18A-18D. GYY4137 dose response and therapeutic treatment on RSV-induced disease and viral replication. (A, B) GYY4137 dose response in vivo. Mice were treated i.n. with different doses of GYY4137 (50 mg, 100 mg, and 200 mg/kg body weight) or an appropriate volume of vehicle (PBS) 1 h before, 6 h and 20 h after infection. Mice were inoculated with either RSV at dose $5\times10^6$ or PBS. (A) Mice were monitored daily and body weight was calculated based on the original weight before the infection. Data are expressed as mean±SEM (n=2-4 mice/group). *$p<0.05$ compared with PBS/RSV at days 2, 3, and 4 post-infection. (B) At day 5 after infection, lungs were excised and viral replication was determined by plaque assay. The bar graph represents mean±SEM (n=2-4 mice/group), *$p<0.0002$, $p<0.0004$, *$p<0.0003$ compared with PBS/RSV group. (C, D) GYY4137 therapeutic in vivo treatment. BALB/c mice were infected with $1\times10^6$ PFU RSV and treated with GYY4137 or vehicle as follows: (1) three doses, at 2 h and at 6 h and 24 h after infection, (2) two doses, one at 6 h and one at 24 h after infection, (3) one dose, at 24 h before infection. (C) Mice were monitored daily and body weight was calculated based on the original weight before the infection. Data are expressed as mean±SEM (n=4 mice/group). *p<0.05 compared with PBS/RSV at days 2, and 3 post-infection. (D) At day 5 after infection, lungs were excised and viral replication was determined by plaque assay. The bar graph represents mean±SEM (n=4 mice/group), *p<0.0003, **p<0.01 compared with PBS/RSV group.

To establish if higher concentration of $H_2S$ donor may be more effective and could further improve RSV-induced disease, increasing doses of GYY4137 (50, 100, and 200 mg/kg body weight) or vehicle were instilled intranasally in mice at 1 h before, 6 h and 24 h after infection. A significant reduction in body weight loss compared to vehicle treatment RSV infected mice was observed for each of the GYY4137 concentration tested (see FIG. 18A). Similarly, clinical disease (estimated by an illness score) appeared to be less severe in GYY4137 treated than vehicle treated RSV-infected mice (data not shown). However, all groups of RSV-infected mice treated with different concentration of GYY4137 showed similar reduction in RSV-induced disease. No differences in body weight loss or illness score were observed in GYY4137 or vehicle treated mock-infected animals (data not shown). Based on the above observations the dose of 50 mg/kg was chosen for subsequent studies on the basis that it was effective and well tolerated by mice.

Figure 18C:
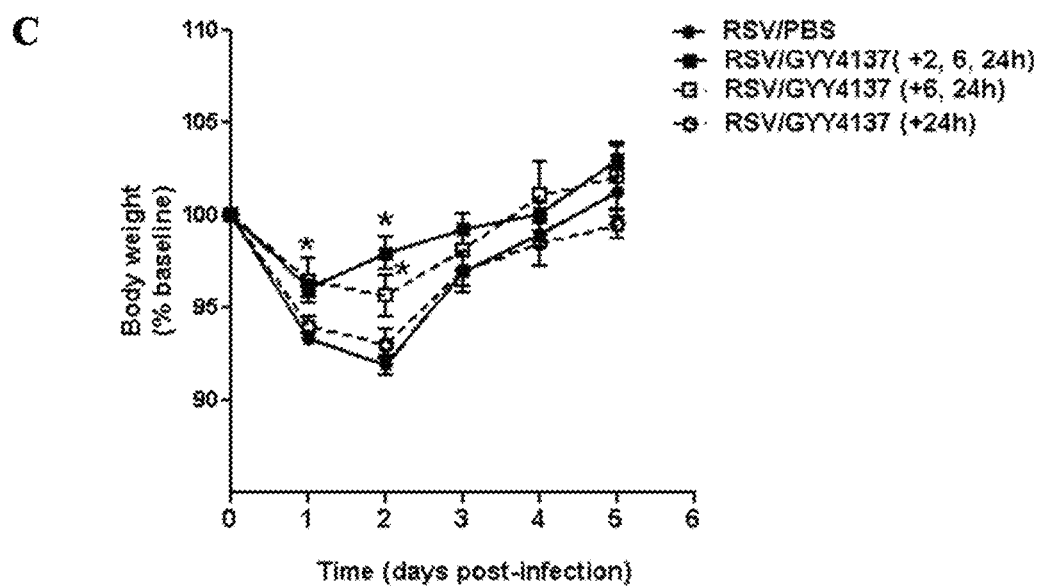

Further experiments were conducted to investigate the "therapeutic" effect of GYY4137 on viral-induced disease. The dose of 50 mg/kg GYY4137 was administered to mice as follow (a) three doses, one at 2 h and at 6 h and 24 h after infection, (b) two doses, one at 6 h and one at 24 h after infection, (c) one dose, at 24 h after infection. Mice were infected with either RSV at dose $1\times10^6$ PFU/mouse or PBS. As shown in FIG. 18C, mice treated with three or two doses of GYY4137 after infection exhibited significantly attenuated RSV-induced body weight loss compared with vehicle treated infected mice. However, when GYY4137 was administered at 24 h post-infection mice exhibited similar body weight loss as compared to vehicle treated infected groups.

Overall, these results suggest that GYY4137 treatment is effective in modulating RSV-induced clinical disease and data were consistent regardless of the size of RSV inoculum used.

It has been shown that RSV infection induces airway hyperresponsiveness (AHR) in response to methacholine challenge. To determine the effect of GYY4137 on pulmonary function, groups of RSV-infected (at dose $1\times10^5$ PFU/mouse) or mock-infected mice under the protocol mentioned above were assessed for AHR in response to methacholine challenge by whole-body barometric plethysmograph (Buxco Electronics, Inc. Sharon, Conn.) at day 5 after infection. Aerosolized methacholine elicited significantly increased AHR in vehicle mice infected with RSV, compared with all other groups. As shown in FIG. 12C, a significant difference between vehicle- and GYY4137-treated RSV-infected animals was observed, since GYY4137 strongly attenuated RSV-induced AHR at administration of higher concentrations of methacholine (25 mg and 50 mg/ml). When compared to vehicle RSV-infected group, GYY4137-treated RSV-infected mice showed approximately two fold decreased in Penh value at dose 50 mg/ml. GYY4137 treatment did not alter baseline Penh values or airway response to methacholine in mock-infected animals.

As shown in FIG. 12D, decreased airway resistance in response to inhaled methacholine in GYY4137 treated RSV infected mice, compared with vehicle RSV infected mice, was confirmed using invasive analysis of lung function on anesthetized mice using the Flexivent system (Scireq, Montreal, Quebec, Canada). Our results show that RSV infected mice treated with GYY4137 exhibited lung resistance values mostly similar to PBS infected animals No differences in lung resistance were observed between the vehicle and GYY4137 mock infected mice. Our preliminary data indicate that treatment with slow-releasing hydrogen sulfide donor, GYY4137, may play a key role in lung function during RSV infection.

GYY4137 Treatment Decreases Pulmonary Inflammation in RSV-Infected Mice.

To investigate whether the effect of GYY4137 treatment could also provide some degree of protection from RSV-induced lung inflammation, we analyzed differential cell count in BAL fluid and determined lung histopathology in RSV-infected mice. Groups of animals were treated with GYY4137 or vehicle and infected i.n. with either RSV or PBS.

Figure 13A:
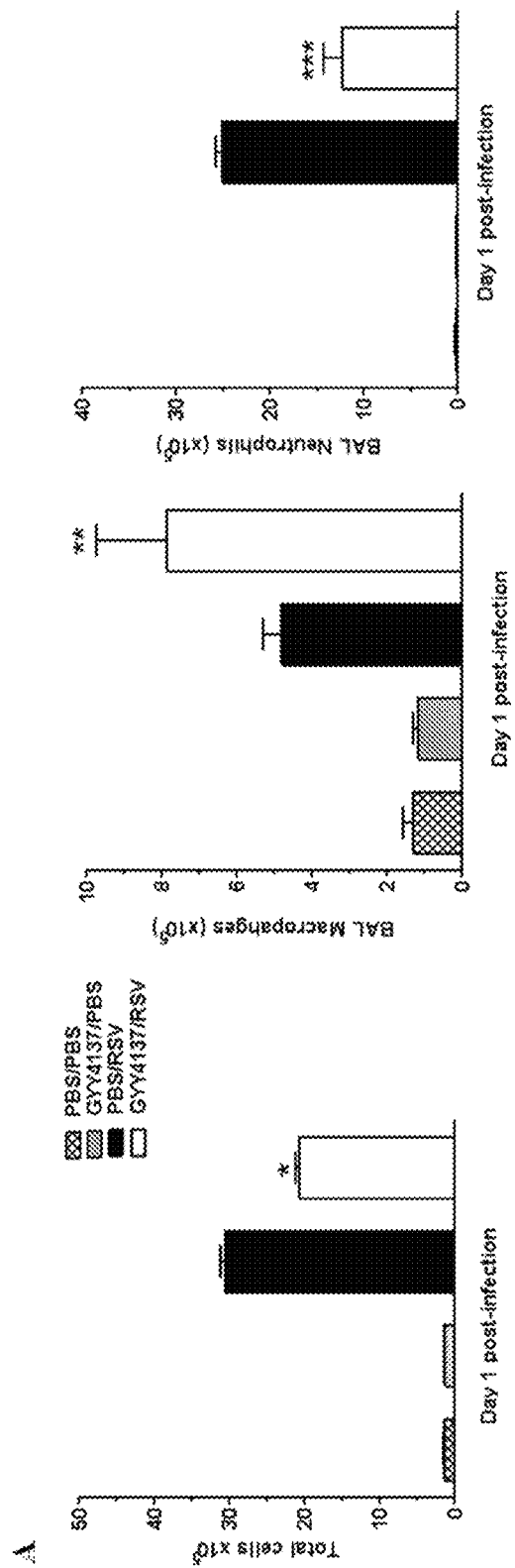
FIG. 13A-13C. Total differential cell counts and pulmonary inflammation in RSV infected mice treated with GYY4137. Mice were treated i.n. with GYY4137 (50 mg/kg body weight) or an appropriate volume of vehicle (PBS) 1 h before, 6 h and 20 h after infection. Mice were inoculated with either RSV or PBS as described in Material and Methods. BAL samples were harvested at day 1 after infection and lung samples for histopathology analysis at day 7 post-infection. (A) Cell preparations were stained (Wright-Giemsa) and counted under the microscope (200 cells/slide). Total and differential cell counts macropahges and neutrophils were determined. The bar graph represents mean±SEM (n=4 mice/group). *$p<0.0001$ compared with PBS/RSV group; $p<0.05$ compared with PBS/RSV group; *$p<0.001$ compared with PBS/RSV group; (B) Lung samples were harvested at day 7 post-infection, fixed for slide preparation and H&E stained. Representative stained lung tissue sections from the indicated treatment. (C) Pathology score of prepared slides (scored as described in Materials and Methods). The bar graph represents mean±SEM (n=4 mice/group). *$p<0.01$ compared with PBS/RSV group.

To characterize the inflammatory cells recruited to the lungs, BAL fluids were obtained from PBS and RSV infected vehicle and GYY4137 treated mice at day 1 after infection. The overall recruitment of inflammatory cells in BAL fluid was significantly reduced for RSV infected GYY4137 treated mice when compared with vehicle RSV infected group (FIG. 13A). BAL fluid from PBS-inoculated vehicle and GYY4137 treated mice consisted mainly of macrophages, whereas RSV infection induces a significant lung recruitment of neutrophils, which become the predominant inflammatory cell observed in the BAL at day 1 post-infection. However, the neutrophils response was significantly decreased for GYY4137 treated mice compared with vehicle ones in response to RSV infection.

Figures 13B, 13C:
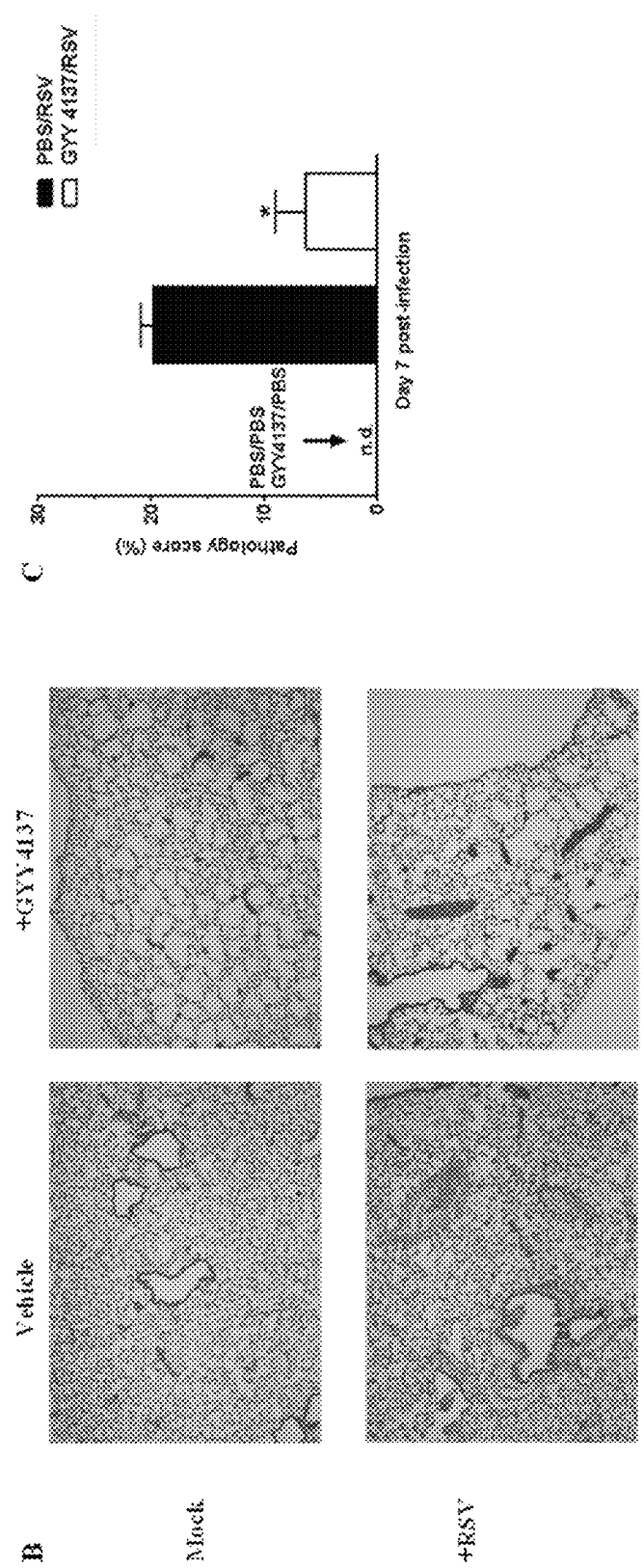

We then analyzed histological changes in the lungs of $H_2S$ donor after RSV infection. Lung tissues from GYY4137- and vehicle-treated mice at day 7 after infection were subjected to H&E staining analysis. Lung histopathology analysis demonstrated that no airway inflammation was observed in mock-infected GYY4137 or vehicle treated animals (FIG. 13B, upper panel). However, in RSV-infected vehicle treated mice, a significant pathology was observed, indicated by an increased cellular infiltration in the alveolar, perivascular, and peribronchoalveolar spaces (FIG. 13B, lower right panel). Compared to sections obtained from GYY4137 treated mice infected with RSV, that response was exacerbated. As shown in FIG. 13C, pathology score indicated that pulmonary inflammation in the GYY4137 treated RSV-infected mice was significantly decreased when compared to vehicle infected animals.

GYY4137 Treatment Alters Cytokines, Chemokines, and Type I IFNs Secretion.

Figure 14:
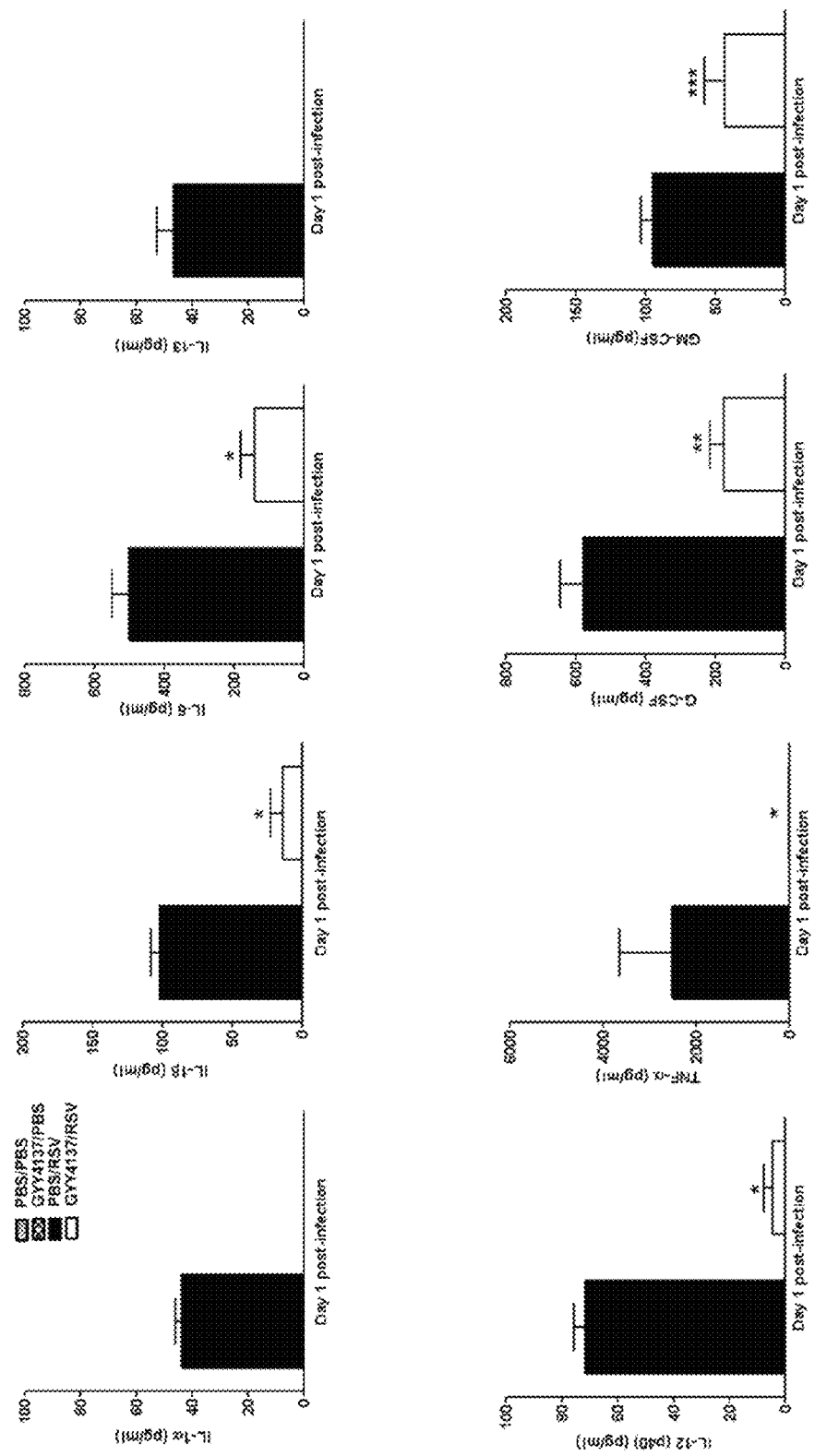
FIG. 14. Effect of GYY4137 on cytokines and growth factors in response to RSV infection. Mice were treated i.n. with GYY4137 (50 mg/kg body weight) or an appropriate volume of vehicle (PBS) 1 h before, 6 h and 20 h after infection. Mice were inoculated with either RSV dose $10^6$ PFU or mock infected. BAL was collected at day 1 after infection to measure cytokines and growth factors by multi-Plex Cytokine detection system. IL-1α, IL-1β, IL-6, IL-13, TNF-α, IL-6. IL-12 p(40), granulocyte-macrophage colony-stimulating factor (GM-CSF), and granulocyte colony-stimulating factor (G-CSF). The bar graph represents mean±SEM (n=3 mice/group). *$p<0.0001$ compared with PBS/RSV group; $p<0.001$ compared with PBS/RSV group; *$p<0.01$ compared with PBS/RSV group.
Figures 15A, 15B:
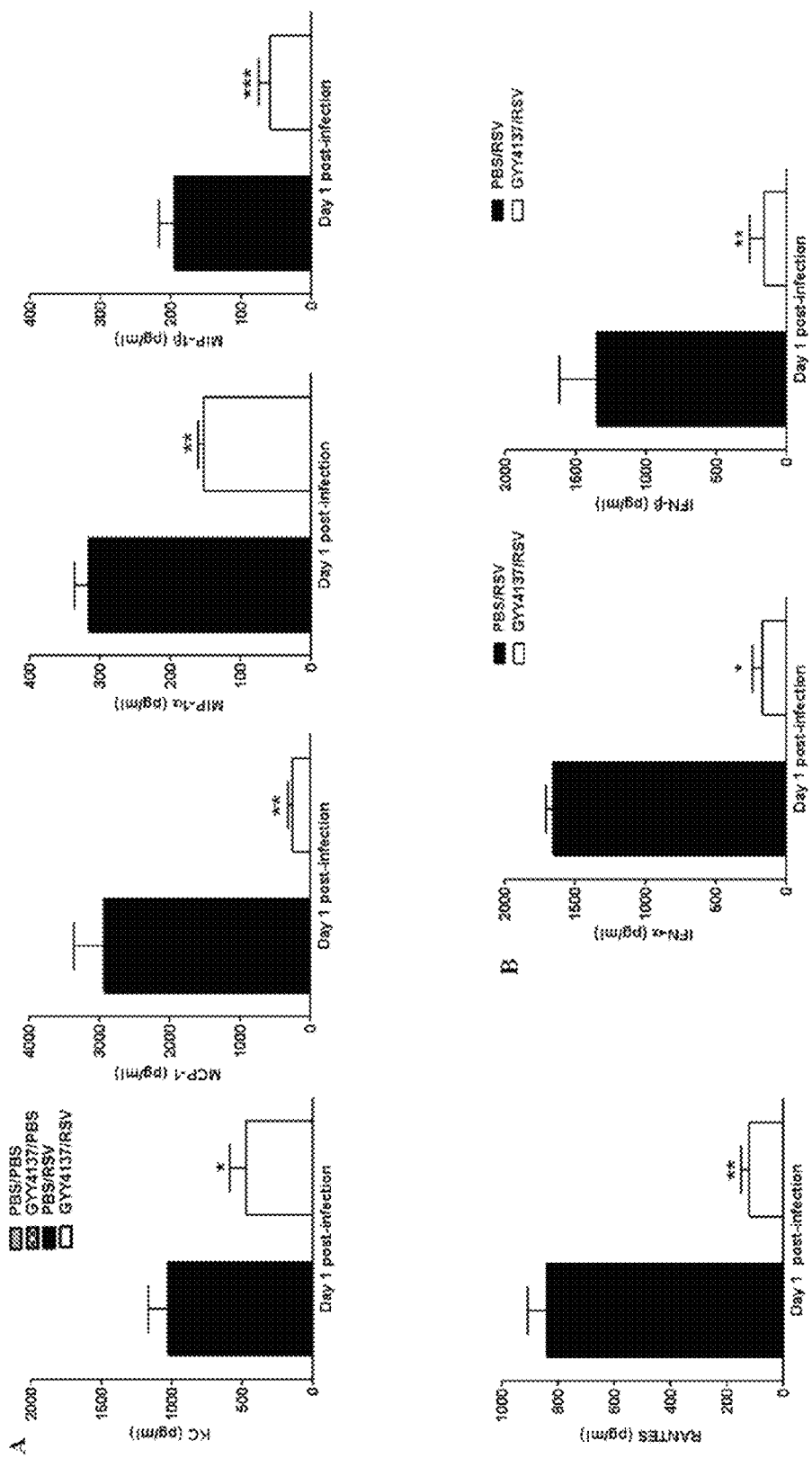
FIG. 15A-15B. Effect of GYY4137 on chemokines and type I IFNs production in response to RSV infection. Mice were treated i.n. with GYY4137 (50 mg/kg body weight) or an appropriate volume of vehicle (PBS) 1 h before, 6 h and 20 h after infection. Mice were inoculated with RSV dose $10^6$ PFU. (A) BAL was collected at day 1 after infection to measure chemokines by multi-Plex Cytokine detection system. The bar graph represents mean±SEM (n=3 mice/group). *$p<0.01$ compared with PBS/RSV group; $p<0.0004$ compared with PBS/RSV group; *$p<0.001$ compared with PBS/RSV group. (B) Levels of IFN-α and INF-β were measured in BAL samples at day 1 after infection by ELISA. The bar graph represents mean±SEM (n=3-4 mice/group). *$p<0.0001$ compared with PBS/RSV group; **$p<0.005$ compared with PBS/RSV group.

To define the effect of GYY4137 in the regulation of RSV-induced cytokine response, the level of cytokines and chemokines was assessed in GYY4137 treated mice and compared to vehicle-treated ones. Mice were treated with GYY4137 or vehicle and infected either with RSV ($1 \times 10^6$ PFU/mouse) or PBS and at day 1 after infection, BAL samples were collected from each group of mice and assessed for the presence of cytokines and chemokines by using Bio-Plex Pro Mouse Group I 23-plex panel detection system. As shown in FIG. 14, the pro-inflammatory cytokines IL-la, IL-1β, IL-6, and TNF-α were differentially induced by vehicle and GYY4137-treated RSV-infected mice. Our data indicate that, compared with vehicle-treated RSV mice, GYY4137 treatment significantly decreased the production of those pro-inflammatory cytokines. In addition, our results showed significantly decreased levels for the granulocyte-macrophage colony-stimulating factor (GM-CSF) and granulocyte-colony stimulating factor (G-CSF) in GYY4137 treated RSV-infected mice. As shown in FIG. 15A, a similar effect was observed in BAL samples from GYY4137 treated RSV-infected mice with the release of the chemokines RANTES, MIP-1α, MIP-1β, MCP-1, and KC.

Figure 19:
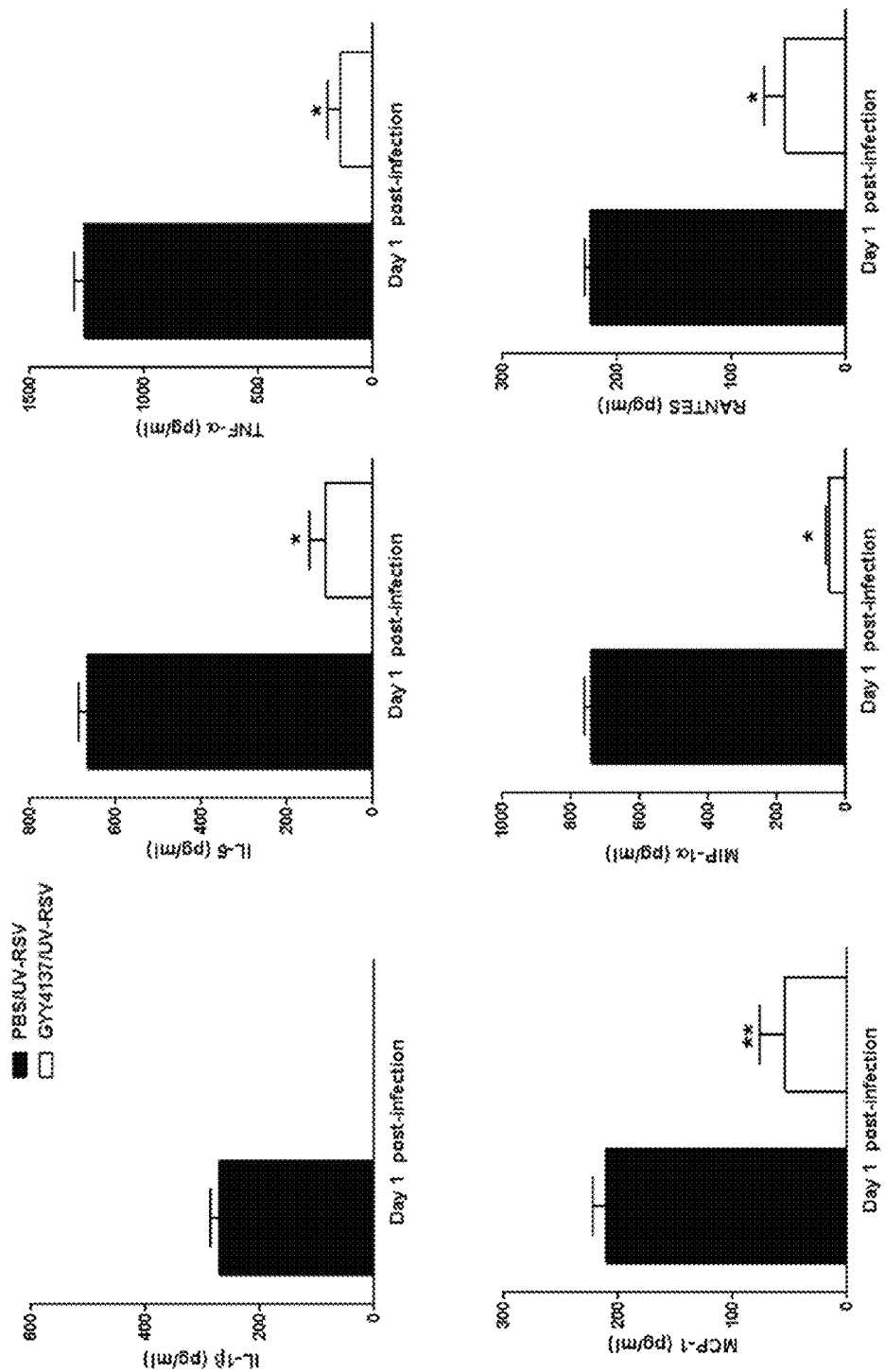
FIG. 19. Effect of GYY4137 on cytokines/chemokine secretion in response to UV-inactivated RSV. Mice were treated i.n. with GYY4137 (50 mg/kg body weight) or an appropriate volume of vehicle (PBS) 1 h before, 6 h and 20 h after infection. Mice were inoculated with either UV-inactivated RSV, dose $1 \times 10^7$ PFU, or mock infected. BAL was collected at day 1 after infection to measure cytokines and chemokines by multi-Plex Cytokine detection system: IL-1β, IL-6, TNF-α, MCP-1, MIP-1β, RANTES. The bar graph represents mean±SEM (n=2-4 mice/group). *p<0.0001 compared with PBS/UV-RSV group; **p<0.0004 compared with PBS/UV-RSV group.

Additionally, mice treated with GYY4137 and infected with UV-inactivated RSV at higher dose of inoculum ($1 \times 10^7$ PFU/mouse) showed a significant decreased on cytokines and chemokines profiles (see FIG. 19) when comparing with vehicle treated mice infected with UV-inactivated virus. Secretion of IL-1β, IL-6, TNF-α, MCP-1, MIP-1β, RANTES were detected for UV-inactivated RSV vehicle treated mice but at significantly lower levels when compared with mice inoculated with live RSV (data not shown for live virus).

Our studies showed that treatment with either GYY4137 or PBS in the non-infected control mice had no effect on the cytokines/chemokines profiles, since the concentrations were below the level of detection assay (data not shown). All together, these data indicate that treatment with GYY4137 exerts a general anti-inflammatory activity in the context of RSV infection of the lung.

It has been shown that RSV can trigger both type I IFN production in vitro and in vivo. We have previously shown that IFN-α/β production peak as early as 24 h after RSV infection, with a rapid decline at 48 h, and by 72 h the amount of IFN-α induced by RSV reached undetectable levels. In the present study, we examined the effect of GYY4137 on the IFN response in mice. Mice were treated with GYY4137 and infected as mentioned above. Based on our previously published studies, BAL samples from all groups were collected after 24 h of infection, and IFN production was measured by ELISA. As shown in FIG. 15B in GYY4137 treaded RSV-infected mice, the IFN-α and IFN-β production was significantly decreased by ~86% and ~84%, respectively when compared with vehicle RSV-infected mice. Overall, these data indicate that administration of exogenous $H_2S$ donor regulates the cytokine response and type I IFN in RSV infected mice.

Treatment with GYY4137 Reduces Viral Replication.

Figures 16A, 16B:
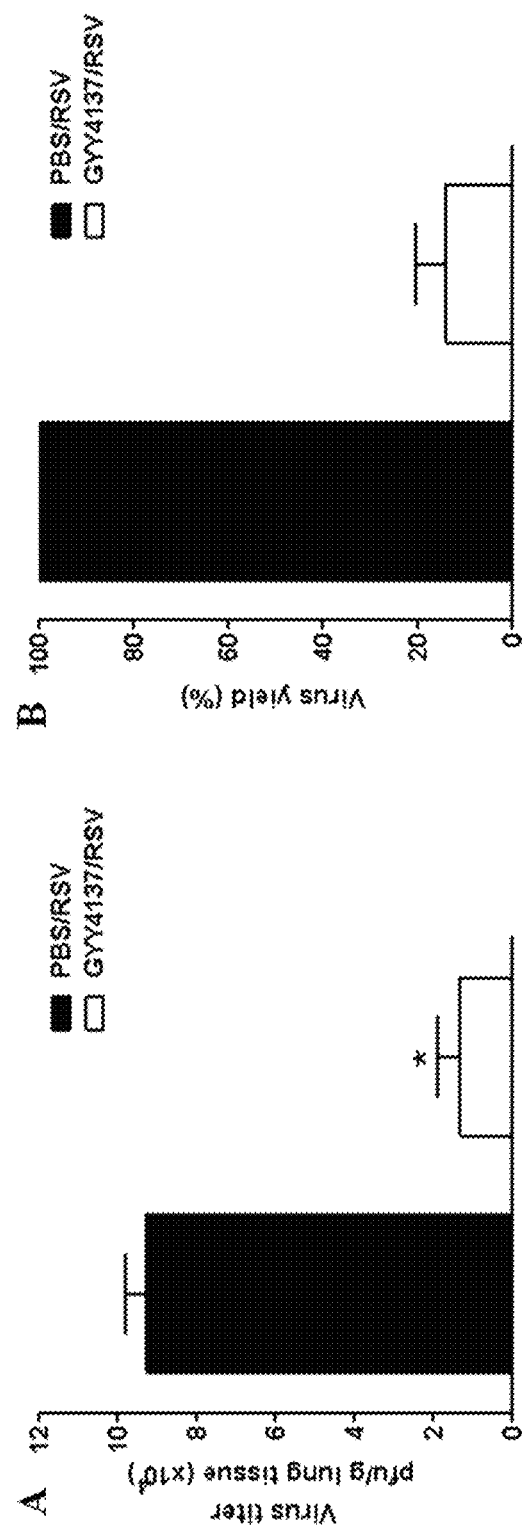
FIG. 16A-16B. GYY4137 treatment reduces viral replication in RSV infected mice. Mice were treated with GYY4137 or vehicle and infected with either RSV or PBS as described in Material and Methods. (A, B) At day 5 after infection, lungs were excised and viral replication was determined by plaque assay. The virus yields of GYY4137 treated RSV infected mice were calculated by setting vehicle treated RSV infected mice values as 100%. The bar graph represents mean±SEM (n=3 mice/group), *$p<0.001$ compared with PBS/RSV group.

To determine whether the attenuation of body weight loss and lung inflammation were related to an altered viral replication in the GYY4137 treated mice, RSV-infected vehicle and GYY4137 treated mice were sacrificed at day 5 after infection (peak viral titer) and total lung tissue was collected to determine virus replication by plaque assay. As shown in FIG. 16A, we observed a significant reduction in viral titers for GYY4137 treated mice compared to vehicle treatment animals, with a reduction of 86% at a dose of 50 mg/kg FIG. 16B). The above experiments demonstrated that treatment with three doses of $H_2S$ donor administered before and after infection has an impact on viral replication.

To evaluate whether increasing concentration of GYY4137 (100 and 200 mg/kg body weight), could further improve viral replication, we treated mice with three doses (1 h before, 6 h and 24 h after infection) of $H_2S$ donor. Our results shows that lower concentration of GYY4137 at 50 mg/kg body weight had an effect that was slightly better than higher ones, at 100 or 200 mg/kg (see FIG. 18B). These data indicate that different concentration of GYY4137 administered in mice were effectively in reducing viral replication as compared with vehicle treated infected animals.

Figure 18D:
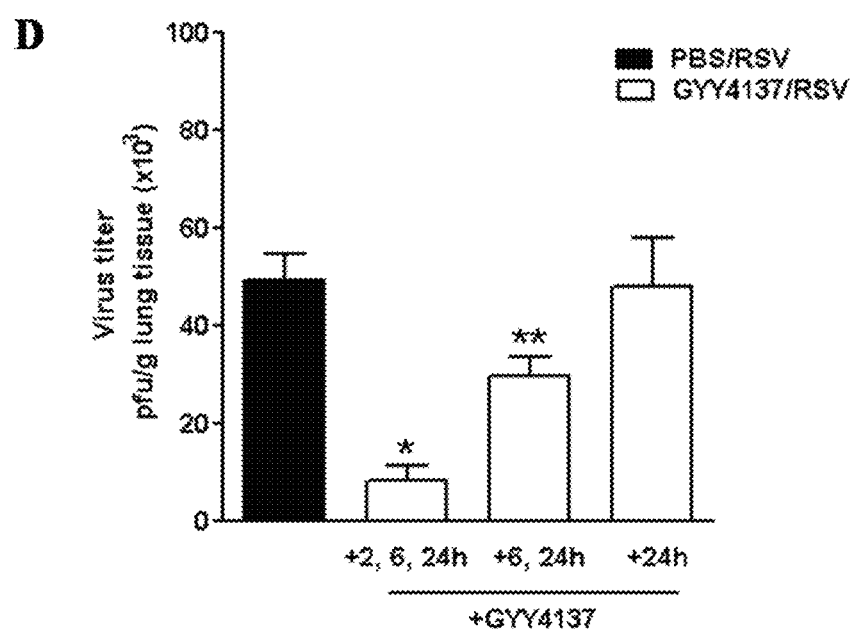

We then tested the ability of the GYY4137 to reduce replication with treatment administered only after infection (therapeutic administration). Based on the above findings the dose of 50 mg/kg was selected for these studies. Mice were infected with RSV and treated with three doses (2 h, 6 h and 24 h after infection), or two doses (6 h and 24 h after infection), or one dose (24 h after infection) of GYY4137 or vehicle. Our results show that three doses of GYY4137 given 2 h, 6 h and 24 h after RSV inoculation or two doses at 6 h and 24 h after infection produced a highly significant reduction of RSV replication, while one dose treatment administered at 24 h after infection produced no further reduction in viral titer as compared with vehicle treated infected mice (see FIG. 18D). The three doses of GYY4137 treatment administered to mice after infection provided approximately similar reduction in viral titer with the three doses of $H_2S$ donor delivered at 1 h before and 6 h and 24 h after infection (FIG. 16B and FIG. 18D). Therefore, the timing of GYY4137 treatment relative to RSV inoculation was a major factor in determining the antiviral efficacy of GYY4137 in this experimental mouse model.

CSE Deficiency Exacerbates Disease Severity, Pulmonary Inflammation and Increases Airway Function and Viral Replication in RSV Infected Mice.

Accumulating evidence has demonstrated that hydrogen sulfide ($H_2S$) is involved in the pathogenesis of various respiratory diseases. Recent studies show that endogenous hydrogen sulfide ($H_2S$) plays an anti-inflammatory role in the pathogenesis of airway inflammation. We have investigated the role of the endogenous cystathionine γ-lyase (CSE)/hydrogen sulfide in the inflammatory and immune responses in an experimentally RSV induced infection by using CSE-deficient mice ($CSE^{-/-}$, referred herein as CSE KO). To confirm the genotype of the CSE KO mice, PCR genotyping was performed using a three-primer assay and gene expression of the three $H_2S$-producing enzymes in the lung was measured. CSE mRNA was absent in the CSE KO mice (data not shown); in contrast, there was no significant difference in the relative mRNA for CBS and 3-MST between WT and CSE KO mice (data not shown).

Figures 17A, 17B, 17C:
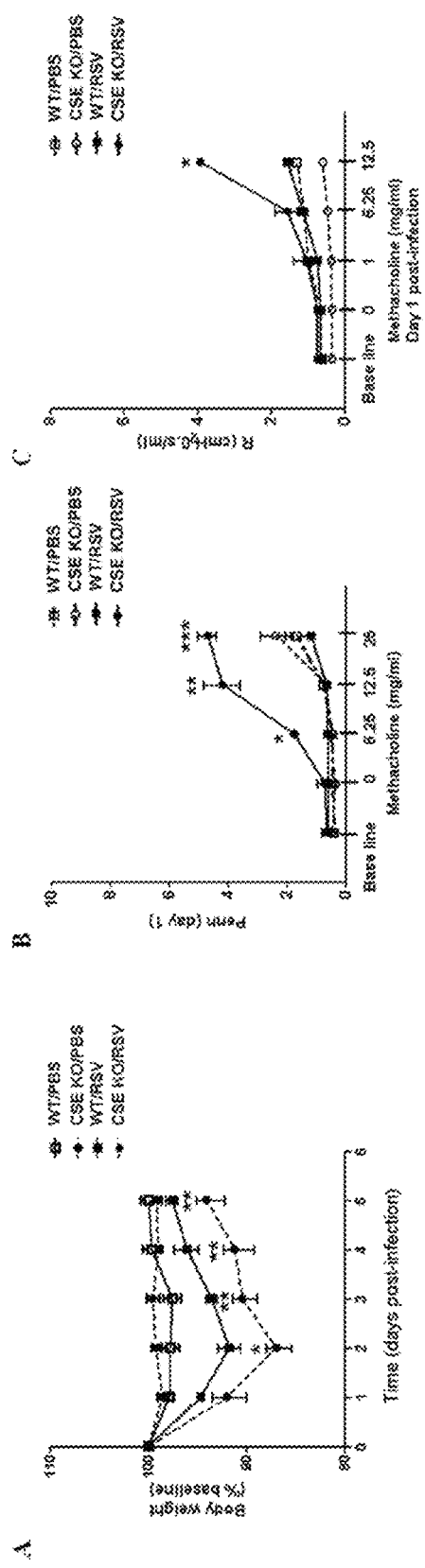
FIG. 17A-17E. RSV infection in CSE deficient mice increases disease severity, pulmonary function, viral replication and lung inflammation. C57BL/6 (WT) and CSE$^{-/-}$ (CSE KO) mice were either infected i.n. with $1\times10^7$ PFU of RSV or PBS. (A) Mice were monitored daily and body weight was calculated based on the original weight before the infection. Data are expressed as mean±SEM (n=3 mice/group). *$p<0.03$ compared with WT/RSV group, **$p<0.04$ compared with WT/RSV group. (B) Unrestrained, whole-body plethysmography (Buxco Electronics, Inc. Sharon, Conn.) was used to measure the Enhanced Pause (Penh) to evaluate AHR. Baseline and post-methacholine challenge Penh values were determined at day 1 after infection. Data are means±SEM (n=3-4 mice/group). * $p<0.0001$ compared with WT/RSV, $p<0.005$ compared with WT/RSV; *$p<0.0006$ compared with WT/RSV, †$p<0.05$ compared with WT/RSV. (C) Airway resistance (day 1 post-infection) measured in mechanically ventilated mice by the Flexivent system. Data are means±SEM (n=3 mice/group). *$p<0.0001$ compared with WT/RSV group. (D) Viral replication in the lungs. At day 5 after infection, lungs were excised and viral replication was determined by plaque assay. The bar graph represents mean±SEM (n=4 mice/group), *$p<0.005$ compared with WT/RSV group. (E) Pathology score of prepared slides (scored as described in Materials and Methods). Lungs were harvested at day 7 after RSV infection, fixed for slide preparation and H&E stained. The bar graph represents mean±SEM (n=4 mice/group). *$p<0.02$ compared with WT/RSV group.

In order to assess whether or not endogenous $H_2S$ has protective effects against RSV-induced disease, we determined a series of parameters, including body weight loss, lung viral titers, histology analysis, and secretion of cytokines and chemokines in CSE KO mice. C57BL/6J (wildtype controls, WT) and CSE KO mice were infected i.n. either with RSV ($1 \times 10^7$ PFU/mouse) or PBS (mock infected), monitored daily, and lung tissue and BAL fluid were analyzed at days 1, 5, and 7 after infection. Body weight loss is a parameter to monitor the severity of the disease after RSV infection. As shown in FIG. 17A, the absence of CSE increased the disease severity of RSV-infected mice. CSE KO mice exhibited more body weight loss (13%) than WT mice (8%) at the peak of the clinical disease at day 2 after infection. Moreover, we observed a delayed recovery to baseline weight in CSE KO RSV-infected mice at days 3, 4 and 5 after infection as compared with WT infected animals. No differences in body weight loss were observed between mock-infected mice.

To investigate the role of CSE deficiency on pulmonary function after RSV infection AHR was assessed by whole-body barometric plethysmograph at day 1 after infection. No differences in baseline Penh values were observed between the WT and CSE KO groups. However, as shown in FIG. 17B, we observed that RSV infected CSE KO mice developed enhanced sensitivity to methacholine challenge, demonstrated by greater Penh values than those of WT infected mice. When compared to WT at day 1 after RSV infection, deficient animals showed significantly increases in Penh values at doses of 6.25, 12.5, and 25 mg/ml of methacholine. Those differences for CSE deficiency in RSV infected mice were observed also when compared to mock-infected groups. We performed additional studies of lung mechanical properties in artificially ventilated mice. As shown in FIG. 17C, no differences in total lung respiratory resistance were observed between the CSE KO and WT groups at concentrations of methacholine of 1 and 6.25. However, we noticed a significantly increase in lung resistance for CSE KO RSV-infected mice at administration of higher concentration of methacholine (12.5 mg/ml). The measurements of lung mechanics in ventilated mice are in agreement with the Penh data observed by unrestrained plethysmography. Based on the present observations, our preliminary data indicate that endogenous cystathionine γ-lyase (CSE)/hydrogen sulfide may play a key role in lung function during RSV infection, as AHR and lung resistance were exacerbated in RSV infected mice in the absence of CSE gene.

Figures 17D, 17E:
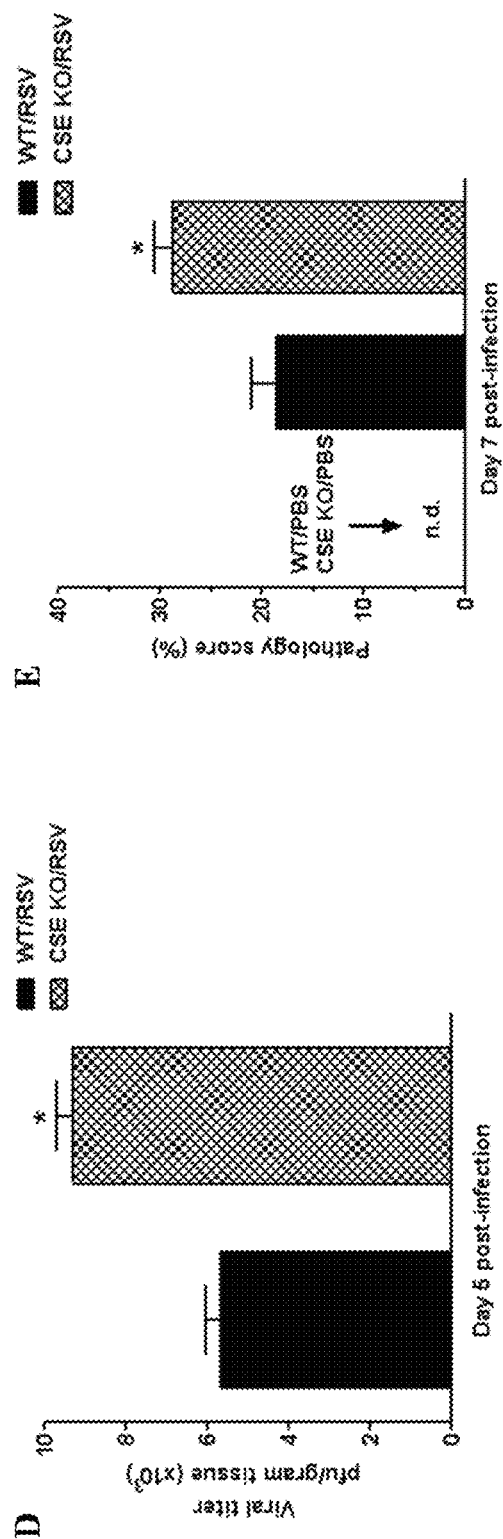

To determine whether the increased of body weight loss was related to changes in viral replication in the deficient mice, RSV-infected CSE KO and WT mice were sacrificed at day 5 after infection and total lung tissue was collected to determine virus replication by plaque assay. As shown in FIG. 17D, RSV replicates in the lungs of WT and CSE KO mice at day 5 after infection. However, our data show that the lack of CSE significantly increased viral titers when compared to WT infected animals.

Next, we determined the role of CSE in the regulation of lung inflammation in response to RSV infection. Differential cell count, cytokines and chemokines secretion in BAL fluid and pathology score were assessed in WT and CSE KO mice. BAL fluid was harvested at days 1, 5, and 7 after infection. Cells from BAL samples were counted, and analyzed for differential cell analysis. At day 1 after RSV infection in the absence of CSE, BAL differential cell counts revealed a significantly increase in the numbers of neutrophils when compared with that of WT mice (data not shown). Numbers of macrophages and lymphocytes were increased at days 5 and 7 after RSV infection, but no significant difference was observed when WT and KO groups of mice were compared (data not shown). Alveolar macrophages were the main cells population from samples of PBS infected mice in both groups of animals.

Figure 20:
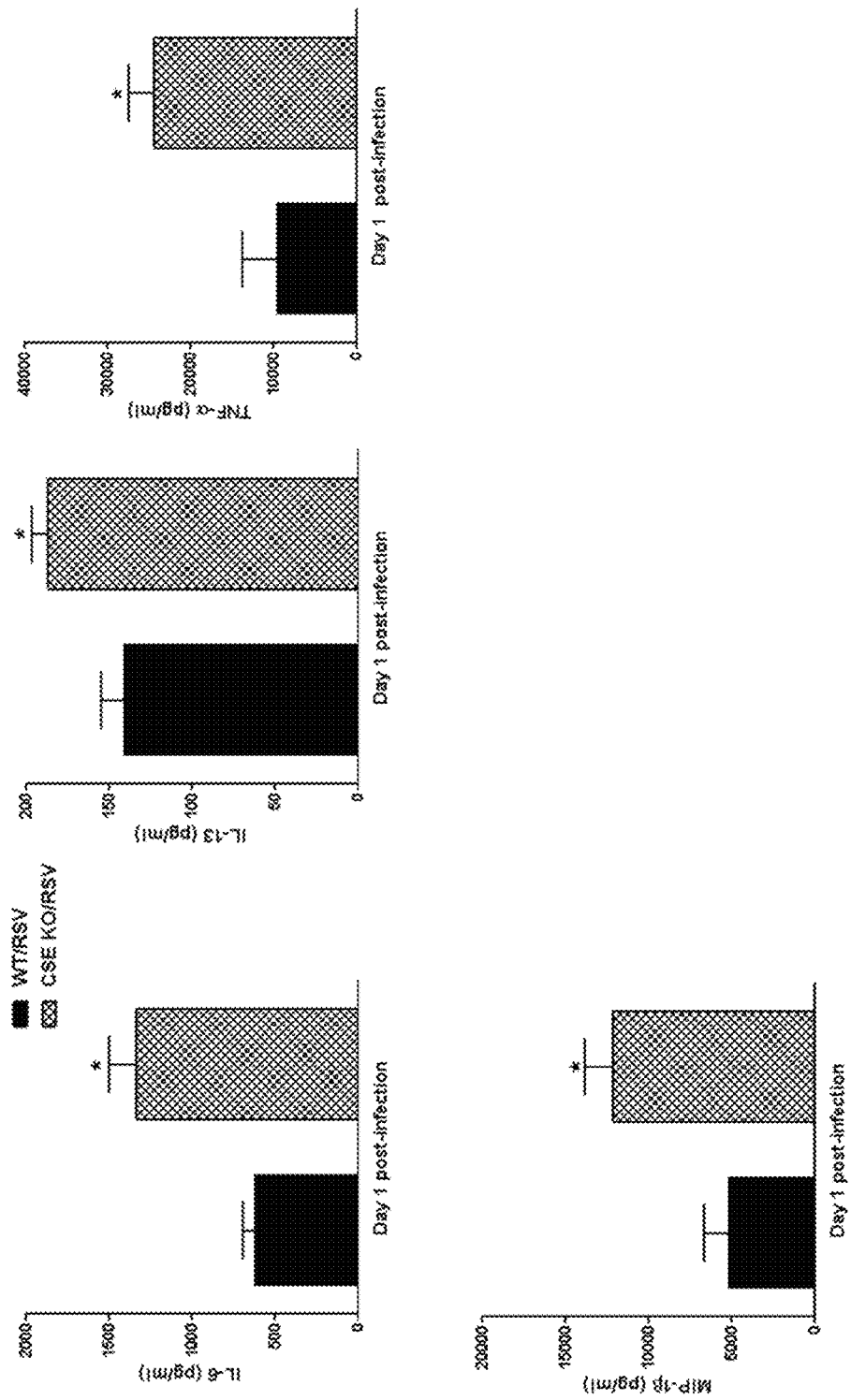
FIG. 20. Cytokine and chemokine production in the lung of CSE KO RSV-infected mice. WT and CSE$^{-/-}$ (CSE KO) mice were infected i.n. with $1 \times 10^7$ PFU of RSV or mock-infected and sacrificed at day 1 after infection. BAL samples were collected from each group of mice and assessed for cytokine/chemokine production by a multi-Plex Cytokine detection system. The bar graph represents mean±SEM (n=3-4 mice/group). *p<0.05 compared with WT/RSV group.

To investigate whether the lack of CSE affected the RSV-induced cytokines and chemokines response, BAL samples collected at day 1 and 5 after infection from each group of mice (CSE KO and WT) were assessed for the presence of cytokines by using a multi-plex cytokine detection system. We found that cytokines and chemokines responses to RSV infection at day 1 were altered in CSE KO mice. Our data indicated that in the absence of CSE, RSV at day 1 after infection induced significant higher levels of cytokines IL-6, IL-13 and TNF-α when compared to WT infected mice (see FIG. 20). A similar effect was observed with the release of chemokines MIP-1β (see FIG. 20), and a trend towards increased for RANTES and MCP-1. However, the levels of cytokines and chemokines for RSV-infected CSE KO and WT mice decreased below the lower limit of detection at day 5 after infection.

For histopathology analysis lung samples were harvested at day 7 post-infection and lung sections were processed and stained for hematoxylin and eosin (H&E). Lung histopathology analysis demonstrated that no airway inflammation was observed in mock-infected WT or CSE KO mice. As shown in FIG. 17D, pathology score indicated that pulmonary inflammation in the CSE KO RSV-infected mice was significantly increased when compared to WT infected animals. RSV infection in the absence of CSE induced exacerbated cellular infiltration characterized by moderate to severe perivasculitis and peribronchiolitis, alveolitis, vasculitis, and scattered syncytia when compared with WT mice.

Overall, the data demonstrated that CSE is involved in the processes of disease severity, lung inflammation, cytokine release and airway hyperresponsiveness in mice experimentally infected with RSV.

Example 3

Figure 21:
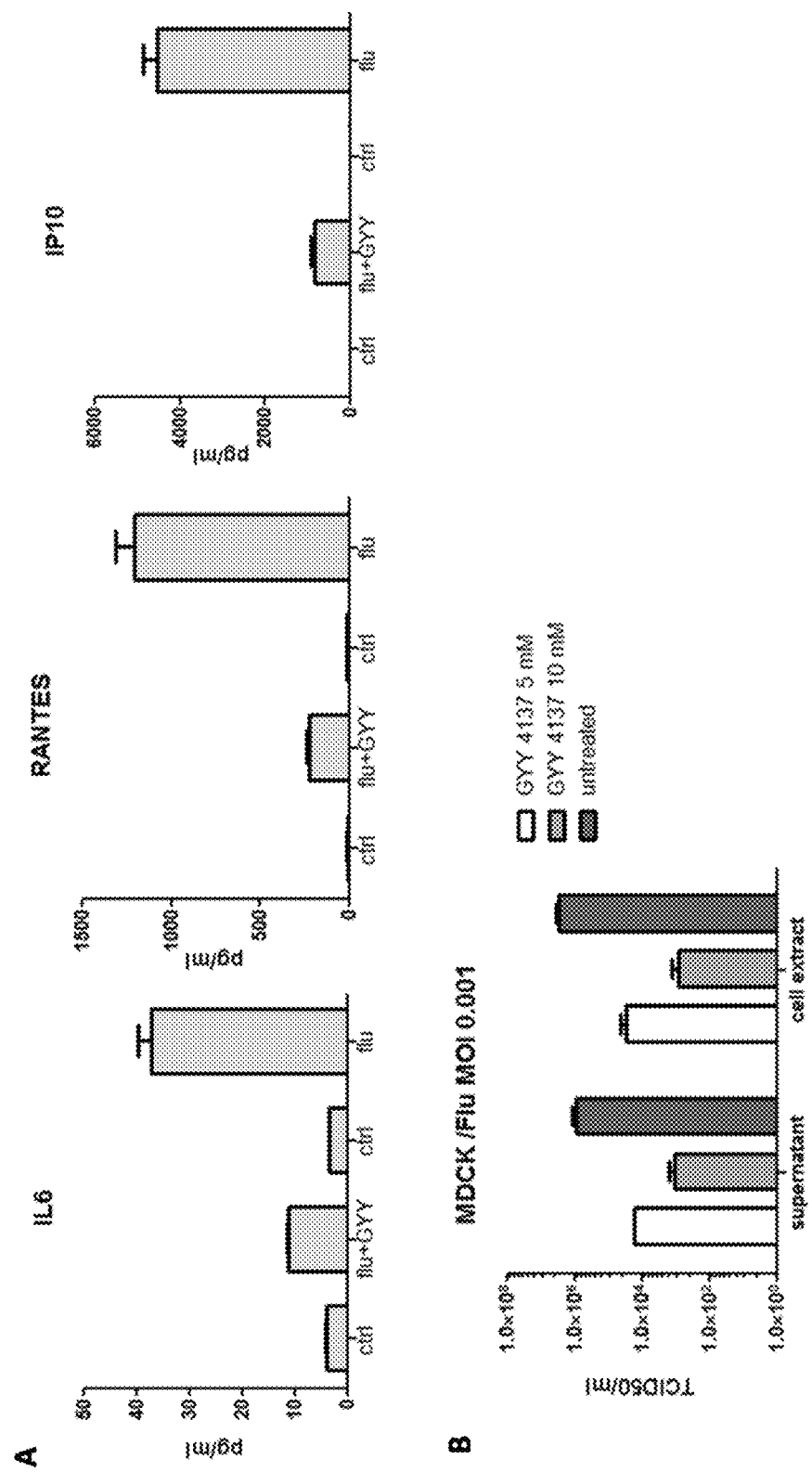
FIG. 21. Effect of $H_2S$ donor treatment on influenza virus (flu) induced chemokine production and viral replication. A549 cells were infected with H1N1 strain of influenza for 1 h followed by treatment with different mM concentrations of GYY4137. (A) Cell supernatants from uninfected and viral-infected, treated or untreated, were assayed at 24 h p.i. for cytokine and chemokine secretion by Bio-Plex. Results are expressed as mean±standard error. (B) Viral replication was determined 24 h post infection by titration of viral infectious particles released in the cell supernatants by TCID50 assay.
Figure 22:
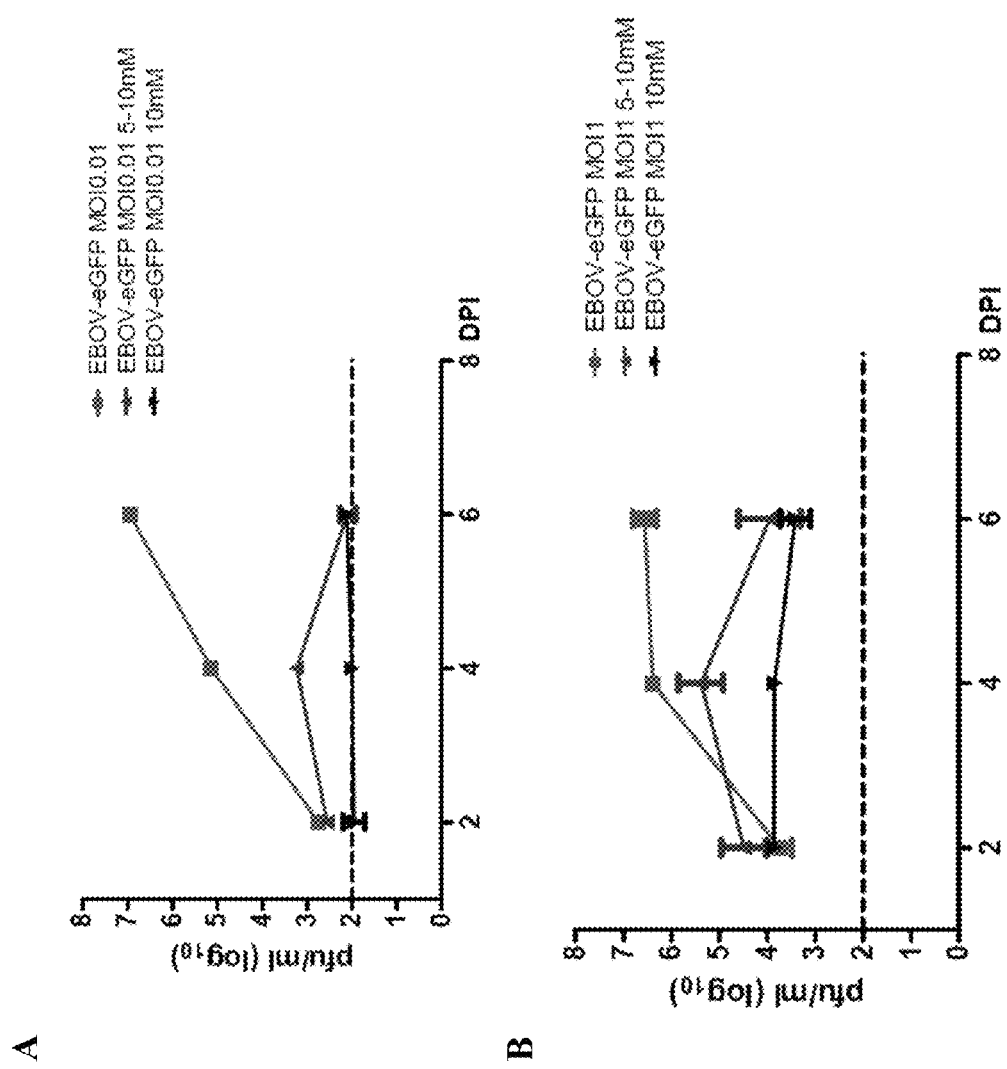
FIG. 22. Effect of $H_2S$ donor treatment on Ebola viral replication. A549 cells were infected with Ebola virus modified to cause expression of enhanced green florescent protein (eGFP) at an MOI of 0.01 (EBOV-eGFP MOI0.01) or 1 (EBOV-eGFP MOI1) for 1 h followed by treatment with 10 mM GYY4137, a kinetic treatment of GYY4137 from 5 mM to 10 mM, or no treatment. Viral replication was determined 2 days, 4 days, and 6 days post infection (DPI) by titration of viral infectious particles released in the cell supernatants and determining the number of plaque forming units (pfu).

Effect of H2S Donor Treatment on Influenza Virus (Flu) Induced Chemokine Production and Viral Replication A549 cells were infected with H1N1 strain of influenza for 1 h followed by treatment with different mM concentrations of GYY4137. (A) Cell supernatants from uninfected and viral-infected, treated or untreated, were assayed at 24 h p.i. for cytokine and chemokine secretion by Bio-Plex. Results are expressed as mean±standard error. (B) Viral replication was determined 24 h post infection by titration of viral infectious particles released in the cell supernatants by TCID50 assay (see FIG. 21).

Example 4

Effect of H2S Donor Treatment on Ebola Viral Replication

Figure 23:
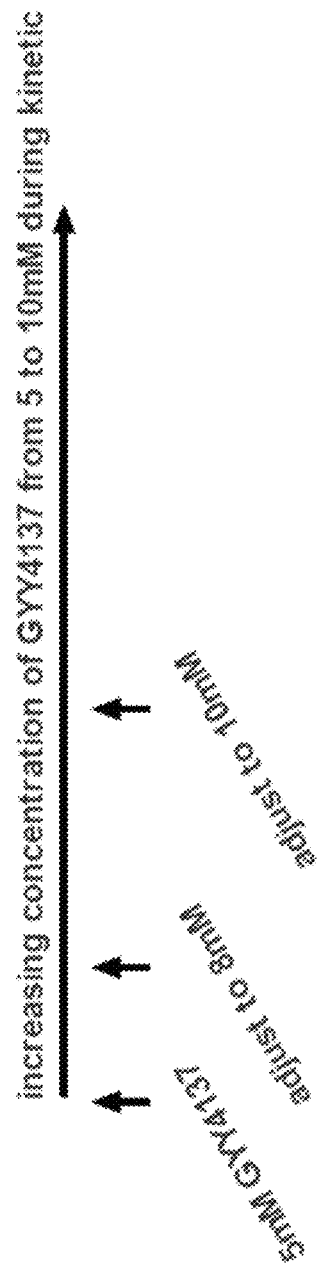
FIG. 23. Kinetic treatment using GYY4137 for increasing concentration of GYY4137 during treatment.

A549 cells were infected with Ebola virus modified to cause expression of enhanced green florescent protein (eGFP) at an MOI of 0.01 (EBOV-eGFP MOI0.01) or 1 (EBOV-eGFP MOI1) for 1 h followed by treatment with 10 mM GYY4137, a kinetic treatment of GYY4137 from 5 mM to 10 mM (FIG. 23), or no treatment. Viral replication was determined 2 days, 4 days, and 6 days post infection (DPI) by titration of viral infectious particles released in the cell supernatants and determining the number of plaque forming units (pfu).

The invention claimed is:

1. A method for treating a filoviridae viral infection of a subject comprising administering an effective amount of an $H_2S$ donor to the subject.

2. The method of claim 1, wherein the viral infection is an Ebola virus infection.

3. The method of claim 1, wherein the $H_2S$ donor is administered by inhalation or inspiration into the respiratory tract.

4. The method of claim 1, wherein the $H_2S$ donor is a slow release $H_2S$ donor.

5. The method of claim 1, wherein the slow release $H_2S$ donor is administered in combination with a fast release $H_2S$ donor.

6. The method of claim 1, wherein the $H_2S$ donor is Gyy4137, ACS67, diallyl trisulfide, NaHS, ATB-343, ATB-337, or AP67.

7. The method of claim 1, wherein the $H_2S$ donor is Gyy4137 or AP67.

* * * * *

UNITED STATES PATENT AND TRADEMARK OFFICE
CERTIFICATE OF CORRECTION

PATENT NO. : 9,504,701 B2
APPLICATION NO. : 14/941340
DATED : November 29, 2016
INVENTOR(S) : Casola et al.

Page 1 of 1

It is certified that error appears in the above-identified patent and that said Letters Patent is hereby corrected as shown below:

In the Specification

Column 1, Lines 11-19, please amend the STATEMENT REGARDING FEDERALLY FUNDED RESEARCH as follows:
This invention was made with government support under AI062885, AI07924602, and P30 ES006676 awarded by the National Institute of Health, and W81XWH1010146 by the Department of Defense. The government may have certain rights to the invention.

Signed and Sealed this
Twentieth Day of March, 2018

Andrei Iancu
*Director of the United States Patent and Trademark Office*